(12) United States Patent
Goren et al.

(10) Patent No.: US 10,655,162 B1
(45) Date of Patent: May 19, 2020

(54) IDENTIFICATION OF BIOMOLECULAR INTERACTIONS

(71) Applicant: The Broad Institute, Inc., Cambridge, MA (US)

(72) Inventors: Alon Goren, Cambridge, MA (US); Robert Nicol, Cambridge, MA (US); Harris Nusbaum, Newton, MA (US)

(73) Assignee: The Broad Institute, Inc., Cambridge, MA (US)

(*) Notice: Subject to any disclaimer, the term of this patent is extended or adjusted under 35 U.S.C. 154(b) by 389 days.

(21) Appl. No.: 15/449,437

(22) Filed: Mar. 3, 2017

Related U.S. Application Data

(60) Provisional application No. 62/303,702, filed on Mar. 4, 2016.

(51) Int. Cl.
```
C12Q 1/6804    (2018.01)
C12Q 1/6869    (2018.01)
G01N 33/68     (2006.01)
G16B 20/30     (2019.01)
```

(52) U.S. Cl.
CPC ......... *C12Q 1/6804* (2013.01); *C12Q 1/6869* (2013.01); *G01N 33/6878* (2013.01); *G16B 20/30* (2019.02)

(58) Field of Classification Search
CPC .................................................. C12N 15/115
See application file for complete search history.

(56) References Cited

U.S. PATENT DOCUMENTS

| | | | | |
|---|---|---|---|---|
| 6,316,229 B1* | 11/2001 | Lizardi | .................. | C12Q 1/682 435/6.1 |
| 8,846,883 B2* | 9/2014 | Brown | .................... | C07H 1/00 435/6.1 |
| 2005/0089893 A1* | 4/2005 | Lopez | .................... | C07H 21/02 435/6.11 |

OTHER PUBLICATIONS

Kowalska et al. Synthesis, properties, and biological activity of boranophosphate analogs of the mRNA cap: versatile tools for manipulation of therapeutically relevant cap-dependent processes. Nucleic Acids Research, vol. 42, No. 16, pp. 10245-1064, Aug. 22, 2014. (Year: 2014).*

Yu et al. Aptamers can discriminate alkaline proteins with high specificity. Chembiochem, vol. 12, No. 17, pp. 2659-2666, Oct. 21, 2011. (Year: 2011).*

Binda, On your histone mark, SET, methylate! Epigenetics. May 2013;8(5):457-63. doi: 10.4161/epi.24451. Epub Apr. 27, 2013.

Boren et al., Ruthenium-catalyzed azide-alkyne cycloaddition: scope and mechanism. J Am Chem Soc. Jul. 16, 2008;130(28):8923-30. doi: 10.1021/ja0749993. Epub Jun. 21, 2008. Erratum in: J Am Chem Soc. Nov. 5, 2008;130(44):14900.

Etchegaray et al., The histone deacetylase SIRT6 controls embryonic stem cell fate via TET-mediated production of 5-hydroxymethylcytosine. Nat Cell Biol. May 2015;17(5):545-57. doi: 10.1038/ncb3147. Epub Apr. 27, 2015.

Goren et al., DNA replication timing of the human beta-globin domain is controlled by histone modification at the origin. Genes Dev. May 15, 2008;22(10):1319-24. doi: 10.1101/gad.468308. Epub Apr. 28, 2008.

Hendrickson et al., High sensitivity multianalyte immunoassay using covalent DNA-labeled antibodies and polymerase chain reaction. Nucleic Acids Res. Feb. 11, 1995;23(3):522-9.

Himo et al., Copper(I)-catalyzed synthesis of azoles. DFT study predicts unprecedented reactivity and intermediates. J Am Chem Soc. Jan. 12, 2005;127(1):210-6.

Jeong et al., Isothermal DNA amplification in vitro: the helicase-dependent amplification system. Cell Mol Life Sci. Oct. 2009;66(20):3325-36. doi: 10.1007/s00018-009-0094-3. Epub Jul. 24, 2009.

Kivioja et al., Counting absolute numbers of molecules using unique molecular identifiers. Nat Methods. Nov. 20, 2011;9(1):72-4. doi: 10.1038/nmeth.1778.

Lara-Astiaso et al., Immunogenetics. Chromatin state dynamics during blood formation. Science. Aug. 22, 2014;345(6199):943-9. doi: 10.1126/science.1256271. Epub Aug. 7, 2014.

Mostoslavsky et al., Asynchronous replication and allelic exclusion in the immune system. Nature. Nov. 8, 2001;414(6860):221-5.

Presolski et al., Copper-Catalyzed Azide-Alkyne Click Chemistry for Bioconjugation. Curr Protoc Chem Biol. 2011;3(4):153-162. Epub Dec. 1, 2011.

Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.

Shishkin et al., Simultaneous generation of many RNA-seq libraries in a single reaction. Nat Methods. Apr. 2015;12(4):323-5. doi: 10.1038/nmeth.3313. Epub Mar. 2, 2015.

* cited by examiner

*Primary Examiner* — Jennifer Dunston
(74) *Attorney, Agent, or Firm* — Wolf, Greenfield & Sacks, P.C.

(57) ABSTRACT

The present disclosure, in some aspects, provides compositions, systems and methods for proximity-based detection of target biomolecules of interest.

15 Claims, 9 Drawing Sheets

Specification includes a Sequence Listing.

Hybridization & strand extension

Denaturation whip-adaptor

↓ *Ligation*

↓ *Hybridization & strand extension*

*Pull down using biotin;
use P2 & P3 for PCR to generate
sequence-ready constructs*

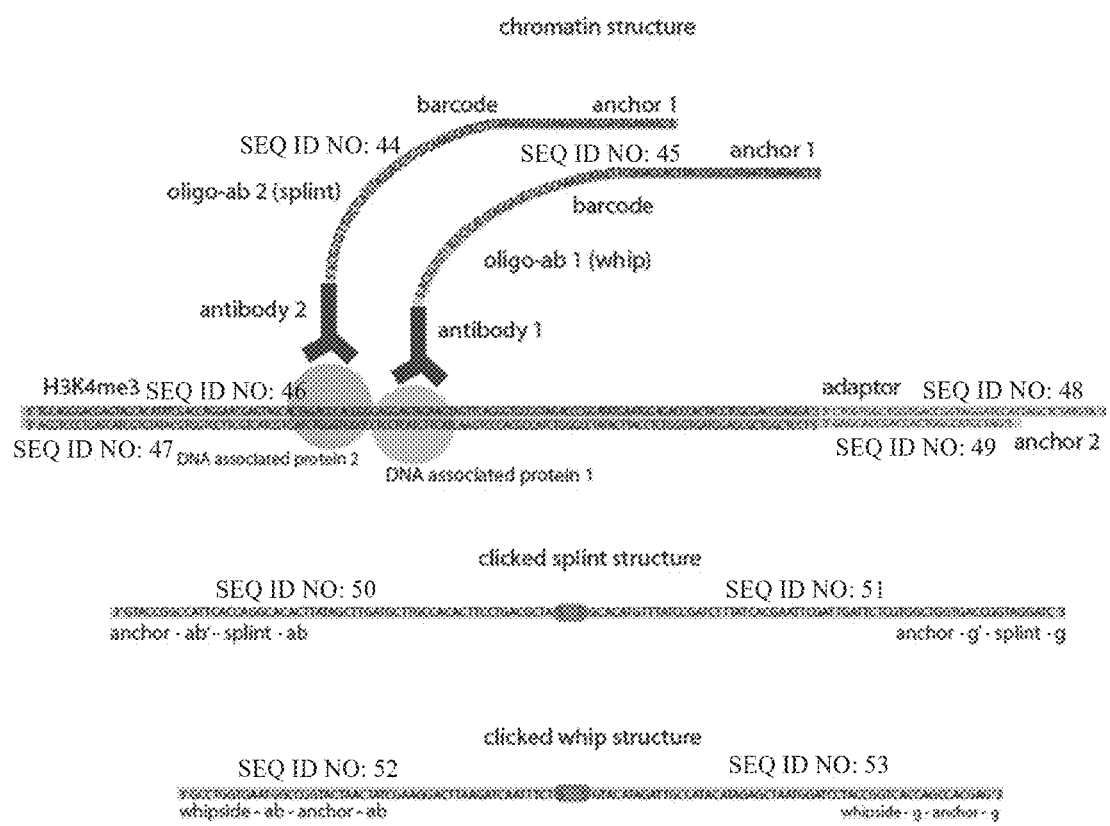

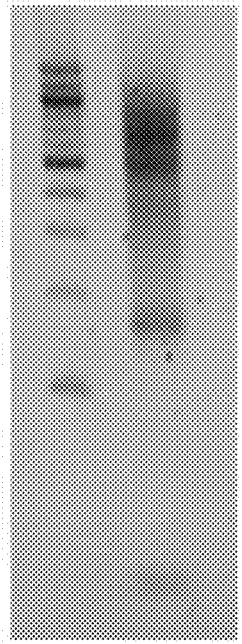 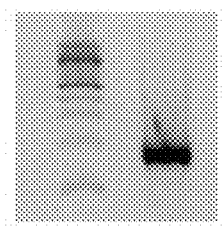 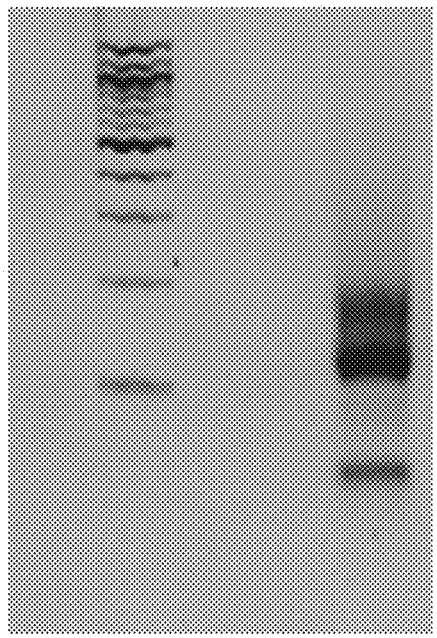
Fig. 7A  Fig. 7B  Fig. 7C
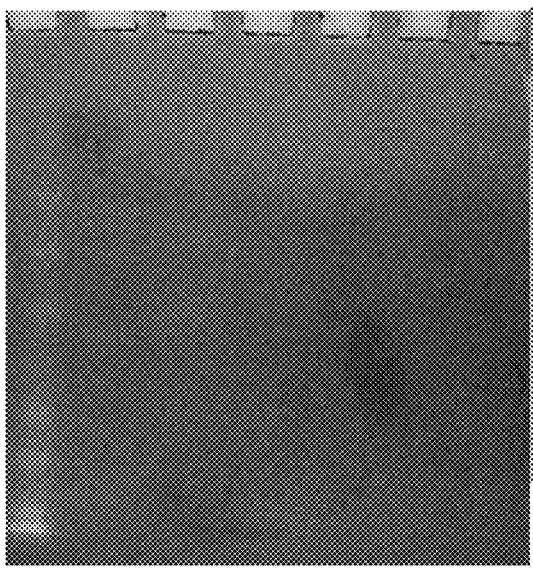 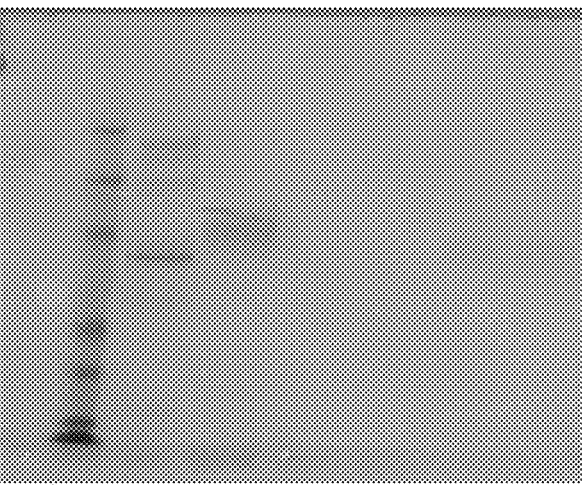
Fig. 8A  Fig. 8B

SEQUENCE LISTING

```
<160> NUMBER OF SEQ ID NOS: 57

<210> SEQ ID NO 1
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 1
tctttaacta gaattcagga agctatcaat catggccggt aagtggtccg         50

<210> SEQ ID NO 2
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 2
gtacatagat tgccatacat agagctaatg gatcctaccg gtcaccagcc acgag    55

<210> SEQ ID NO 3
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 3
atcgcagtcc ttcacaccgt tctgtagttc gatattcaca cggaccactt accggccatg   60

<210> SEQ ID NO 4
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 4
gcacatgttt atccgatctt tatcacgaat tcgattgatt ctcgtggctg gtgaccggta   60
ggatc                                                              65

<210> SEQ ID NO 5
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (12)..(13)
<223> OTHER INFORMATION: Modified by a phosphothioate bond

<400> SEQUENCE: 5
accagccacg agt                                                     13

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
taccggtcac cagccacgag                                              20
```

```
<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
gatcctaccg gtcaccagcc                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
taatggatcc taccggtcac                                          20

<210> SEQ ID NO 9
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 9
tctttaacta gaattcagga agctatcaat                                30

<210> SEQ ID NO 10
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 10
gtacatagat tgccatacat agagctaatg                                30

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
catggccggt aagtggtccg                                          20

<210> SEQ ID NO 12
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 12
gatcctaccg gtcaccagcc acgag                                    25

<210> SEQ ID NO 13
<211> LENGTH: 30
<212> TYPE: DNA
<213> ORGANISM: Artificial Sequence
<220> FEATURE:
```

```
<223> OTHER INFORMATION: Synthetic Polynucleotide

<400> SEQUENCE: 13
ttcacaccga tctgtagatc aatgatcaga                                30

<210> SEQ ID NO 14
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 14
atccaacctt tatcacgaat tcgattgatt                                30

<210> SEQ ID NO 15
<211> LENGTH: 6
<212> TYPE: DNA
<213> ORGANISM: Artificial Sequence
<220> FEATURE:
<223> OTHER INFORMATION: Synthetic Polynucleotide

<400> SEQUENCE: 15 gaattc                                                          6

<210> SEQ ID NO 16
<211> LENGTH: 4
<212> TYPE: DNA
<213> ORGANISM: Artificial Sequence
<220> FEATURE:
<223> OTHER INFORMATION: Synthetic Polynucleotide

<400> SEQUENCE: 16 ccgg                                                            4

<210> SEQ ID NO 17
<211> LENGTH: 6
<212> TYPE: DNA
<213> ORGANISM: Artificial Sequence
<220> FEATURE:
<223> OTHER INFORMATION: Synthetic Polynucleotide

<400> SEQUENCE: 17 aagctt                                                          6

<210> SEQ ID NO 18
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 18
tctttaacta gaattcagga agctatcaat catggccggt aagtggtccg          50

<210> SEQ ID NO 19
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 19
gtacatagat tgccatacat agagctaatg gatcctaccg gtcaccagcc acgag    55
```

```
<210> SEQ ID NO 20
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 20
atcgcagtcc ttcacaccgt tctgtagttc gatattcaca cggaccactt accggccatg     60

<210> SEQ ID NO 21
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 21
gcacatgttt atccgatctt tatcacgaat tcgattgatt ctcgtggctg gtgaccggta     60
ggatc                                                                 65

<210> SEQ ID NO 22
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 22
tctttaacta gaattcagga agctatcaat                                      30

<210> SEQ ID NO 23
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 23
gtacatagat tgccatacat agagctaatg                                      30

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
catggccggt aagtggtccg                                                 20

<210> SEQ ID NO 25
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 25
gatcctaccg gtcaccagcc acgag                                           25

<210> SEQ ID NO 26
<211> LENGTH: 50
<212> TYPE: DNA
<213> ORGANISM: Artificial Sequence
<220> FEATURE:
```

```
<223> OTHER INFORMATION: Synthetic Polynucleotide

<400> SEQUENCE: 26
tctttaacta gaattcagga agctatcaat catggccggt aagtggtccg          50

<210> SEQ ID NO 27
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 27
gtacatagat tgccatacat agagctaatg gatcctaccg gtcaccagcc acgag    55

<210> SEQ ID NO 28
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 28
ctcgtggctg gtgaccggta ggatccatta                                30

<210> SEQ ID NO 29
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (12)..(13)
<223> OTHER INFORMATION: Modified by a phosphothioate bond

<400> SEQUENCE: 29
accagccacg agt                                                  13

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 30
taccggtcac cagccacgag                                           20

<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 31
gatcctaccg gtcaccagcc                                           20

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
```
taatggatcc taccggtcac                                          20

<210> SEQ ID NO 33
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 33
actgtgtttg tctcatgtag gaggtgcgca aagcatactt cggaccactt accggccatg    60
attgatagct                                                           70

<210> SEQ ID NO 34
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 34
tctttaacta gaattcagga agctatcaat catggccggt aagtggtccg               50

<210> SEQ ID NO 35
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 35
gtacatagat tgccatacat agagctaatg gatcctaccg gtcaccagcc acgag         55

<210> SEQ ID NO 36
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 36
ctcgtggctg gtgaccggta ggatccatta gctctatgta                          40

<210> SEQ ID NO 37
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 37
gatcctaccg gtcaccagcc acgag                                          25

<210> SEQ ID NO 38
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 38
tgcagggacg agtagcacat atcgaccagg aacgagtagc actagaccca ccgggaggag    60
tagaagtagt tcagggtgcg gtagacccgg atatgaatgg agaccactac cctcgcgacc   120
gagga        125

<210> SEQ ID NO 39
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 39
tcctcggtcg cgaggtagtg ggtctccatt catatccggg tctaccgcac cctgaactac        60
ttctactcct cccggtgggt ctagtgctac tgcttcctgg tgcatatgtg ctactagtcc        120
ctgca        125

<210> SEQ ID NO 40
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 40
tgcgcacctc ctacatgaga cccgcgctta gggggg        36

<210> SEQ ID NO 41
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 41
taagcgcggg tctcatgtag gaggtgcgca        30

<210> SEQ ID NO 42
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 42
tctttaacta gaattcagga agctatcaat catggccggt aagtggtccg        50

<210> SEQ ID NO 43
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 43
gtacatagat tgccatacat agagctaatg gatcctaccg gtcaccagcc acgagccccc        60
c        61

<210> SEQ ID NO 44
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 44
actgtgtttg tctcatgtag gaggtgcgca aagcatactt catggccggt aagtggtccg        60

```
<210> SEQ ID NO 45
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 45
actgtgtttg tctcatgtag gaggtgcgcg aaagcatact tcggaccact taccggccat    60
gattgatagc t                                                         71

<210> SEQ ID NO 46
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 46
tgcagggacg agtagcacat atcgaccagg aacgagtagc actagaccca ccgggaggag    60
tagaagtagt tcagggtgcg gtagacccgg atatgaatgg agaccacta cctcgcgacc   120 gagga                                                               125

<210> SEQ ID NO 47
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 47
tcctcggtcg cgaggtagtg ggtctccatt catatccggg tctaccgcac cctgaactac    60
ttctactcct cccggtgggt ctagtgctac tgcttcctgg tgcatatgtg ctactagtcc   120
ctgca                                                               125

<210> SEQ ID NO 48
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 48
ctcgtggctg gtgaccggta ggatccatta gctctatgta                          40

<210> SEQ ID NO 49
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 49
gatcctaccg gtcaccagcc acgag                                          25

<210> SEQ ID NO 50
<211> LENGTH: 59
<212> TYPE: DNA
<213> ORGANISM: Artificial Sequence
<220> FEATURE:
```

(preceding continuation)
```
tgtgaatatc                                                           70
```

<223> OTHER INFORMATION: Synthetic Polynucleotide

<400> SEQUENCE: 50
atcgcagtcc ttcacaccgt tcgtagttcg atattcacac ggaccactta ccggccatg    59

<210> SEQ ID NO 51
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 51
gcacatgttt atccgatctt tatcacgaat tcgattgatt ctcgtggctg gtgaccggta    60
ggatc    65

<210> SEQ ID NO 52
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 52
tctttaacta gaattcagga agctatcaat catggccggt aagtggtccg    50

<210> SEQ ID NO 53
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 53
gtacatagat tgccatacat agagctaatg gatcctaccg gtcaccagcc acgag    55

<210> SEQ ID NO 54
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 54
gtacatagat tgccatacat agagctaatg gatcctaccg gtcaccagcc acgag    55

<210> SEQ ID NO 55
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 55
ctcgtggctg gtgaccggta ggatccatta gctctatgta tggcaatcta tgtac    55

<210> SEQ ID NO 56
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 56
ctcgtggctg gtgaccggta ggatccatta gctctatgta tggcaatcat atgtacagaa    60

```
attgatctta agtccttcga tagttagtac cggccattca ccaggcagac tagtaactag        120
atgtctagcc acacttatcc aacctttatc acgaattcga ttgatt                      166

<210> SEQ ID NO 57
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 57
aatcaatcga attcgtgata aaggttggat aagtgtggct agacatctag ttactagtct         60
gcctggtgaa tggccggtac taactatcga aggacttaag atcaatttct gtacatatga        120
ttgccataca tagagctaat ggatcctacc ggtcaccagc cacgag                       166
```

IDENTIFICATION OF BIOMOLECULAR INTERACTIONS

RELATED APPLICATION

This application claims the benefit under 35 U.S.C. § 119(e) of U.S. provisional application No. 62/303,702, filed Mar. 4, 2016, which is incorporated by reference herein in its entirety.

SEQUENCE LISTING

The sequence listing created as an ASCII text file on Mar. 3, 2017, having a size of 12.8 KB, and entitled B119570041US00-SEQ-HJD is incorporated herein by reference.

BACKGROUND

Mapping the genomic organization of modified histones and defining locations of deoxyribonucleic acid (DNA) binding proteins is important for understanding the regulatory mechanisms governing cellular states. The primary methodology used for mapping DNA associated proteins—chromatin immunoprecipitation followed by sequencing (ChIP-seq)—has several major limitations: (i) the ChIP-seq signal is effectively an average derived from a population of cells due to chromatin input requirements; (ii) standard ChIP-seq is unable to profile more than one epitope at one time in one sample; and (iii) the immunoprecipitation step is inefficient, resulting in signal reduction.

SUMMARY

Provided herein is a technology that can be used, in some aspects, to simultaneously study the organization of multiple DNA-binding proteins from a single sample and to identify instances where these proteins are bound to the same genomic molecule originating from a single cell, enabling multiplex genomic localization of multiple DNA-associated proteins from a single sample, for example. The simultaneous interrogation of DNA-associated proteins in an individual sample enables the inference of protein complex dynamics with high sensitivity. The system, methods and compositions of the present disclosure, in some embodiments, avoid immunoprecipitation altogether through the use of long specialized nucleic acids (referred to as whip molecules) and DNA barcoding (present in, for example, barcoded nucleic acids). Thus, the systems, methods and compositions, in some embodiments, provide a simple, rapid, low-cost means to address many previously unanswerable questions in chromatin biology and other biological fields. For example, the technology provided herein enables analysis of the different combinatorial signatures of chromatin regulators, the dynamics of their formation during differentiation, and how these signatures may go awry in disease. The high-resolution mapping in turn serves as a guide, in some instances, for designing therapeutic approaches targeting disease.

Some aspects of the present disclosure provide a single-stranded nucleic acid comprising two 3' ends, referred to herein as a whip molecule. It should be understood that whip molecules are non-naturally occurring, engineered nucleic acids. In some embodiments, the single-stranded nucleic acid is a conjugate comprising a first nucleic acid strand comprising a 5' end linked to a 5' end of a second nucleic acid strand. In some embodiments, the 5' end of the first nucleic acid strand is covalently linked to the 5' end of the second nucleic acid strand. In some embodiments, the 5' end of the first nucleic acid strand comprises an azide group and the 5' end of the second nucleic acid strand comprises an alkyne group. Other means of joining two 5' ends of nucleic acids are encompassed herein. For example, any variation of "click chemistry," as discussed below, may be used in accordance with the present disclosure.

In some embodiments, the single-stranded nucleic acid (or nucleic acid conjugate) whip has a length of 10-1000 nucleotides.

Some aspects of the present disclosure provide biomolecule detection systems (or kits) comprising (a) a (at least one) single-stranded nucleic acid comprising two 3' ends, wherein one 3' end comprises a first anchor domain and the other 3' end comprises a second anchor domain, and (b) a (at least one) barcoded nucleic acid comprising a primer domain, a barcode domain and a nucleotide domain that is complementary to the first anchor domain of the single-stranded nucleic acid of (a).

In some embodiments, the single-stranded nucleic acid is a conjugate comprising a first nucleic acid strand comprising a 5' end linked to a 5' end of a second nucleic acid strand. In some embodiments, the 5' end of the first nucleic acid strand is covalently linked to the 5' end of the second nucleic acid strand. In some embodiments, the 5' end of the first nucleic acid strand comprises an azide group and the 5' end of the second nucleic acid strand comprises an alkyne group. As indicated above, other means of joining two 5' ends of nucleic acids are encompassed herein.

In some embodiments, the single-stranded nucleic acid of (a) comprises two 5' primer domains. These primer domains may be used, for example, to amplify and/or sequence a barcoded construct produced by the methods as provided herein.

In some embodiments, the biomolecule detection systems further comprise at least one nucleic acid adaptor that comprises (i) a unique molecular identifier (UMI) and (ii) a nucleotide domain that is complementary to the second anchor domain of the single-stranded nucleic acid of (a). Adaptor molecules are used, in some embodiments, to append specific to a nucleic acid (e.g., to a barcoded nucleic acid or a target biomolecule). An adaptor molecule may include a UMI or other unique sequence, or an adaptor molecule may include an anchor domain containing a nucleotide sequence complementary to one 3' end of a whip molecule.

In some embodiments, the biomolecule detection systems further comprise a (at least one) binding biomolecule that binds to a target biomolecule of interest. The binding biomolecule may be, for example, a nucleic acid or a protein. In some embodiments, the binding biomolecule is a protein, such as, for example, an antibody.

In some embodiments, the target biomolecule is a histone.

In some embodiments, the biomolecule detection systems further comprise a polymerase (DNA polymerase or RNA polymerase).

In some embodiments, the biomolecule detection systems further comprise a nucleic acid adaptor that comprises (i) a paired nucleotide sequence flanked by (ii) an unpaired primer domain similar to the primer domain of the barcoded nucleic acid and (iii) an unpaired homopolymer domain. In some embodiments, the nucleic acid adaptor is linked to biotin.

In some embodiments, the biomolecule detection systems further comprise a ligase.

In some embodiments, the biomolecule detection systems further comprise a terminal transferase (e.g., terminal deoxynucleotidyl transferase) or another enzyme capable of adding nucleotides to a 3' end of a whip molecule.

In some embodiments, the biomolecule detection systems further comprise a pair of primers, wherein one of the primers is complementary to one of the primer domains of the single-stranded nucleic acid, and the other primer is complementary to the other primer domain of the single-stranded nucleic acid. As indicated above, the primers may be used, for example, to sequence a barcoded construct produced by a method of the present disclosure.

In some embodiments, the systems further comprise at least two barcoded nucleic acids, wherein each barcoded nucleic acid comprises a primer domain, a barcode domain and a nucleotide domain that is complementary to the first anchor domain of the single-stranded nucleic acid of (a).

Some aspects of the present disclosure provide methods that comprise: combining in reaction solution (e.g., buffer) that comprises polymerase and nucleoside triphosphates (e.g., deoxynucleoside triphosphates (dNTPs)) (a) a single-stranded nucleic acid comprising two 3' ends, wherein each 3' end comprises an anchor domain, (b) a barcoded nucleic acid comprising a primer domain, a barcode domain and a nucleotide domain that is complementary to one of the anchor domains of the single-stranded nucleic acid, wherein the barcoded nucleic acid is linked to a binding biomolecule that binds to a target biomolecule of interest, and (c) a biomolecule comprising a nucleotide domain that is complementary to the other of the anchor domains of the single-stranded nucleic acid, thereby forming a reaction mixture; and incubating the reaction mixture under conditions that result in binding of the single-stranded nucleic acid of (a) to the barcoded nucleic acid of (b) and to the biomolecule of (c), and extension (polymerization) of the single-stranded-nucleic acid through the primer domain of the barcoded nucleic acid, thereby producing a partially-double-stranded molecule.

In some embodiments, the methods further comprise incubating in reaction solution the partially-double-stranded molecule under conditions (e.g., denaturation/melting conditions) that result in separation of the partially-double-stranded molecule into a barcoded nucleic acid and an extended single-stranded nucleic acid comprising a complementary barcode domain (complementary to the barcode domain of the barcoded nucleic acid) and a complementary primer domain (complementary to the primer domain of the barcoded nucleic acid), wherein the extended single-stranded nucleic acid comprises two 3' ends.

In some embodiments, the methods further comprise incubating in reaction solution that comprises ligase the extended single-stranded nucleic acid and a nucleic acid adaptor that comprises (i) a paired nucleotide sequence flanked by (ii) an unpaired primer domain that binds to the complementary primer domain of the extended single-stranded nucleic acid and (iii) an unpaired homopolymer domain (e.g., a GGGG-domain), under conditions that result in ligation of the nucleic acid adaptor to the extended single-stranded nucleic acid, thereby producing a partially-double-stranded nucleic acid comprising a homopolymer domain at one of the 3' ends of the extended single-stranded nucleic acid.

In some embodiments, the methods further comprise incubating in reaction solution that comprises a terminal transferase the partially-double-stranded nucleic acid comprising a homopolymer domain, under conditions that results in addition of deoxynucleotides (e.g., CCCC-) to the other 3' end of the extended single-stranded nucleic acid to produce a homopolymer domain at the other 3' end of the extended single-stranded nucleic acid, wherein the two homopolymers domains of the single-stranded nucleic acid are complementary to each other, thereby forming a second reaction mixture.

In some embodiments, the methods further comprise incubating the second reaction mixture in the presence of polymerase and dNTPs under conditions that result in nucleic acid hybridization and polymerization for a time sufficient to produce a circular, double-stranded nucleic acid comprising a barcode domain (a barcoded construct produced by the method).

In some embodiments, the methods further comprise incubating in reaction solution the circular, double-stranded nucleic acid under conditions that result in linearization of the circular, double-stranded nucleic acid, thereby producing a linear double-stranded nucleic acid comprising a barcode domain.

In some embodiments, the methods further comprise sequencing the linear double-stranded nucleic acid. The sequence information may be used, for example, to determine the identity of target biomolecules within close proximity (e.g., 500 nm or less) of one another.

BRIEF DESCRIPTION OF THE DRAWINGS

FIG. 3, top schematic, shows two different barcoded nucleic acids, each linked to an antibody that is bound to a cognate DNA-associated protein (e.g. histone) located on a fragment of genomic DNA. The middle schematic shows an example of a clicked splint structure (two nucleic acids joined through a click chemistry reaction), which may be used to verify the yield of click chemistry and/or to show that a particular whip molecule is functioning as expected (e.g., binding to the intended anchor domains).

FIG. 4A shows that cross-linked chromatin was immobilized with an antibody targeting H3K27ac, then ligated to adaptors (e.g., ILLUMINA®), and the ~400 bp product (~200 bp mono-nucleosomes and 180 bp of adaptors) was then amplified by PCR. From left to right: 100 bp ladder; ligated and amplified chromatin; original sheared chromatin (~200 bp, mononucleosomes). FIG. 4B shows a representative view from the IGV browser demonstrating the similarity between data generated by chromatin ligation (bottom) and by ChIP-seq (top) from the same mouse embryonic stem (ES) cells. FIG. 4C shows a genome-wide analysis demonstrating high correlation ($R2=0.75$) between read coverage in peak regions as generated by chromatin ligation and ChIP-seq.

FIG. 7A shows an image of a gel showing a 100 base pair (bp) ladder (left lane) and a 187 bp fragment, which is the PCR product (right lane). The lower band is the primer. The higher bands are non-specific products. FIG. 7B shows an image of a gel showing the 187 fragment (IS plus adapters) after gel extraction and PCR amplification using "primer-adaptor2." FIG. 7C shows an image of a gel showing the 187 fragment (IS plus adapters) cut by TaqaI. The resulting fragments are 134 bp and 53 bp. The band above is the uncut 187 bp fragment. IS: Internal Standards (see U.S. Pat. No. 9,175,043, incorporated herein by reference).

FIGS. 8A-8B show images of a polyacrylamide gel electrophoresis (PAGE) stained both for DNA (left) and proteins (right).

DETAILED DESCRIPTION

Provided herein, in some aspects, is a technology referred to as "Whip-seq," which enables the simultaneous mapping of multiple DNA-associated proteins from a single sample, greatly reduces sample input requirements, and detects proteins that are bound to the same original in vivo genomic region. The methods and systems of the present disclosure use a single-stranded nucleic acid (e.g., DNA) molecule having two 3' ends. This molecule is referred to herein as a "whip molecule." This molecule may be produced, in some embodiments, by linking (e.g., covalently bonding) the 5' ends of two nucleic acids using, for example, azide-alkyne "click" chemistry (Presolski et al. *Curr Protoc Chem Biol* 3, 153-162 (2011)). Other chemical or biological linkages may be used, as discussed below. The whip molecule functions, in some embodiments, as a proximity detector, capable of detecting biomolecules within close proximity to each other. To enable the multiplex genomic localization of proteins from a single sample, including proteins localized to the same genomic molecule, for example, the methods of the present disclosure use a combination of barcoding technologies (see, e.g., Hendrickson et al. *Nucleic Acids Res* 23, 522-9 (1995)).

The technology provided herein, in some embodiments, may be used in many applications that require convention immunoprecipitation and/or proximity ligation. While the present disclosure primarily exemplifies use of the Whip-seq technology for immunoprecipitation-based applications, it should be understood that this technology is not so limited. For example, a whip molecule may be used to identify any pair of biomolecules (e.g., nucleic acids, proteins, or other molecules) that physically co-localize or come within close proximity to each other. Thus, the technology provided herein may be used, for example, to study cell surface interactions, nucleic acid (e.g., DNA-RNA or DNA-DNA) interactions, or co-localization of mRNA transcripts (e.g., in secretory vesicles, exosomes or mRNA particles). Other applications are encompassed by the present disclosure.

Figure 1A:
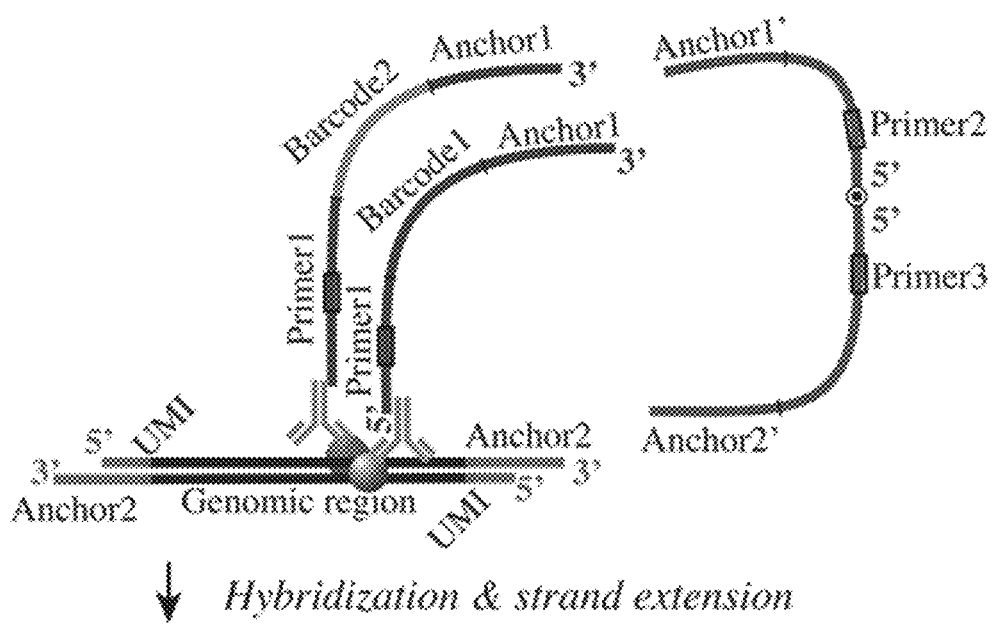
FIGS. 1A-1G show an example of mapping the genomic localization of multiple proteins in vivo using Whip-seq. The figures illustrate the major steps of an example Whip-seq reaction. Abbreviations: Anc—Anchor; B—Biotin; Bc—Barcode; Gr—Genomic region; P—Primer; U—UMI; *—Cleavable blocker; ( )—a gap.
Figure 1B:
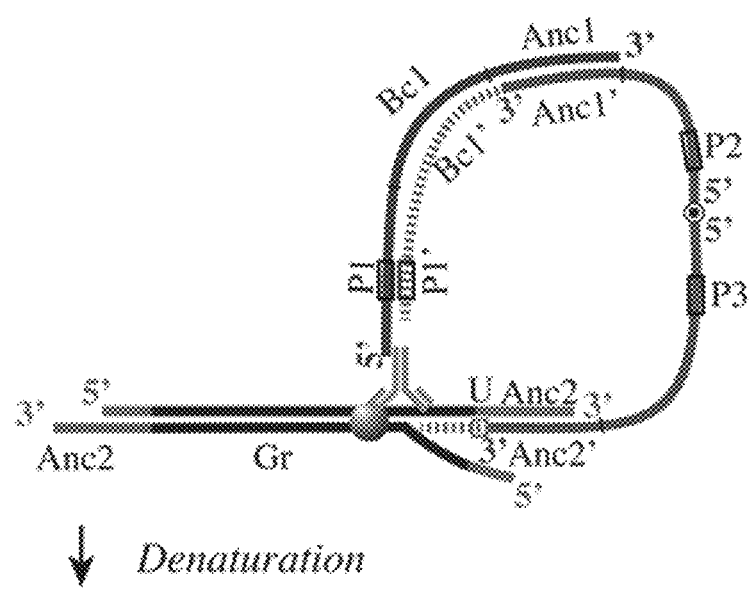
Figure 1C:
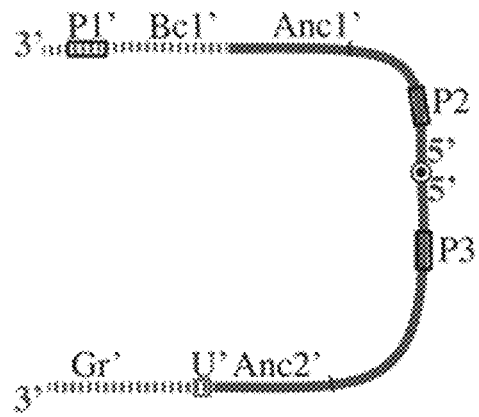

An overview of an example of a method of the present disclosure for detecting a region of chromatin and a DNA-associated protein within close proximity of each other is schematized in FIGS. 1A-1G, proceeding as follows. (i) First, cellular chromatin is cross-linked to covalently bind associated proteins to the DNA. The cross-linked genomic DNA is then sheared and ligated to adaptors; each adaptor contains a unique molecular identifier (UMI) and a single-stranded overhang region complementary to the anchor site (Anchor 2) for the right arm of the whip (Anchor 2'; the whip is the molecule to the right of the figure) (FIG. 1A). (ii) Next, antibodies to the desired epitopes are bound to the cross-linked chromatin constructs. To enable the multiplexed interrogation of DNA binding proteins, each specific antibody is marked with a covalently-linked single-stranded barcoded nucleic acid. This is done, for example, using commercially available kits (e.g., Antibody-Nucleic acid All-in-One Conjugation Kit, SOLULINK™). This barcoded nucleic acid contains three elements: an anchor sequence (Anchor 1) complementary to the left arm of the whip (Anchor 1'), an antibody-specific barcode and a primer domain (P1) that is utilized in subsequent steps (FIG. 1A). (iii) Next, the whip is used to capture the sequences of both the nucleic acid linked to the antibody and the associated genomic region by 3' polymerase extension (FIG. 1B). The whip anchor domains are hybridized to the complementary anchor domains located on the barcoded nucleic acid linked to the antibody and on the adaptor ligated to the genomic chromatin fragment. Then the two 3' ends of the hybridized whip each act as priming sites for DNA polymerase extension; this extension covalently captures the sequences of the antibody tag and the associated genomic region. (iv) Next, the extended whip is dissociated (e.g., denatured) from the chromatin and then ligated to a biotinylated partially double-stranded whip-adaptor. It should be understood that biotin is one example of a molecule that may be linked to the whip adaptor. Other binding partner molecules are encompassed by the present disclosure (e.g., ligands, receptors). The whip-adaptor provides intramolecular annealing of the extended whip (FIG. 1C-E), so that it can be resolved into a molecule amenable to DNA sequencing. (v) Lastly, via self-annealing and another round of DNA extension, biotin pull-down (or other molecular pull-down) and PCR, the extended whip is converted into a sequence-ready construct (FIG. 1F-1G). By sequencing libraries generated in this manner, genomic regions associated with the specific proteins targeted by the barcoded antibodies can be identified. The UMIs enable unambiguous identification of instances where the multiple barcoded nucleic acids (Whip-seq tags) originated from the same genomic molecule. Whip-seq transforms the mapping of chromatin, for example, into a highly sensitive, inexpensive and robust process. The technology provided herein, in some aspects, does not require specialized equipment, so it can be carried out in any molecular biology laboratory.

Single-Stranded Nucleic Acid Whip

Provided herein is a single-stranded nucleic acid comprising two 3' ends (referred to as a whip molecule). A nucleic acid (a polymer of nucleotides) is "single-stranded" if nucleotides that form the nucleic acid are unpaired. That is, nucleotides of a single-stranded nucleic acid are not base paired (via Watson-Crick base pairs, e.g., guanine-cytosine and adenine-thymine/uracil) to nucleotides of another nucleic acid. A single-stranded nucleic acid may be contrasted with a double-stranded (paired) nucleic acid, a typical example of which is a DNA double helix. Single-stranded nucleic acids may include a contiguous (uninterrupted) sequence of nucleotides or, in some embodiments, a single-stranded nucleic acid may be a conjugate that includes two nucleic acid strands joined together, for example, through a chemical (covalent) linkage.

In nature, a single strand of a nucleic acid (e.g., DNA or RNA) has a 5' end (five prime end) and a 3' end (three prime end). The 5' end typically contains a phosphate group attached to the 5' carbon of the ribose ring of a nucleotide and a 3' end, which is unmodified from the ribose —OH substituent. Nucleic acids are synthesized in vivo in the 5' to 3' direction. Polymerase relies on the energy produced by breaking nucleoside triphosphate bonds to attach new nucleoside monophosphates to the 3'-hydroxyl (—OH) group, via a phosphodiester bond.

An engineered single-stranded nucleic acid of the present disclosure has two 3' ends (a whip molecule). Each terminus of the single-stranded nucleic acid includes a 3'-hydroxyl (—OH) group. In some embodiments, a single-stranded whip molecule is formed by joining (linking) the 5' end of one single-stranded nucleic acid to the 5' end of another single-stranded nucleic acid, as shown, for example, in FIG. 1A, right image, and in FIG. 3, bottom image ("clicked whip structure"). In some embodiments, the linkage between two 5' ends is a covalent linkage. In other embodiments, the linkage is noncovalent.

The 5' ends of single-stranded nucleic acids may be linked to each other using any means in the art for linking nucleic acids to each other. In some embodiments, nucleic acids are linked together using 'click chemistry' (see, e.g., V. V. Rostovtsev et al. *Angew. Chem. Int. Ed.,* 2002, 41, 2596-2599; F. Himo et al. *J. Am. Chem. Soc.,* 2005, 127, 210-216; and B. C. Boren et al. *J. Am. Chem. Soc.,* 2008, 130, 8923-8930). An example of a click chemistry reaction is the Huisgen 1,3-dipolar cycloaddition of alkynes to azides to form 1,4-disubstituted-1,2,3-triazoles. The copper(I)-catalyzed reaction is mild and very efficient, requiring no protecting groups, and requiring no purification, in many cases. The azide and alkyne functional groups are largely inert towards biological molecules and aqueous environments, which allows the use of the Huisgen 1,3-dipolar cycloaddition in target-guided synthesis and activity-based protein profiling. Thus, in some embodiments, a whip molecule is formed by linking the 5' end of one nucleic acid strand that includes an azide group to the 5' end of another nucleic acid strand that includes an alkyne group. Other linkage reactions are encompassed by the present disclosure and are known in the art.

The length of a single-stranded nucleic acid whip molecule may vary. In some embodiments, the length of a whip molecule is 10-1000 nucleotides. For example, a whip molecule may have a length of 10-900, 10-800, 10-700, 10-600, 10-500, 10-400, 10-300, 10-200, 10-100, 10-50 or 10-25 nucleotides. In some embodiments, a whip molecule has a length of 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 450 or 500 nucleotides. In some embodiments, a whip molecule is longer than 1000 nucleotides. In some embodiments, the length of a whip molecule is $10^3$, $10^4$, $10^5$ or $10^6$ nucleotides.

Single-stranded nucleic acid whip molecules typically include an "anchor domain" at each 3' end. A "domain" refers to a discrete, contiguous sequence of nucleotides or nucleotide base pairs, depending on whether the domain is unpaired (single-stranded nucleotides) or paired (double-stranded nucleotide base pairs), respectively. Complementary anchor domains bind to each other. A domain is "complementary to" another domain if one domain contains nucleotides that base pair (hybridize/bind through Watson-Crick nucleotide base pairing) with nucleotides of the other domain such that the two domains form a paired (double-stranded) or partially-paired molecular species/structure. Complementary domains need not be perfectly (100%) complementary to form a paired structure, although perfect complementarity is provided, in some embodiments. Thus, an anchor domain of a whip molecule that is complementary to an anchor domain of a barcoded nucleic acid (described below) binds to that domain, for example, for a time sufficient to initiate polymerization in the presence of polymerase and under conditions appropriate for polymerization. FIG. 1B, for example, shows anchor domain, Anc 1', of a whip molecule binding to a complementary anchor domain, Anc 1, of a barcoded nucleic acid, and anchor domain, Anc 2,' of the same whip molecule binding to a complementary anchor domain, Anc 2, of genomic DNA.

The length of an anchor domain may vary. In some embodiments, an anchor domain has a length of 5-50 nucleotides. For example, an anchor domain may have a length of 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-40, 25-35, 25-30, 30-40, 30-35 or 35-40 nucleotides. In some embodiments, an anchor domain has a length of 5, 10, 15, 20, 25, 30, 35, 40, 45 or 50 nucleotides. In some embodiments, an anchor domain has a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. An anchor domain, in some embodiments, is longer than 50 nucleotides, or shorter than 5 nucleotides.

In some embodiments, a single-stranded nucleic acid whip molecule comprises primer domains. A primer domain is a domain to which a primer binds. A primer is a strand of short nucleotide sequence that serves as a starting point for nucleic acid (e.g., DNA) synthesis. In some embodiments, whip molecules comprises a pair of internal primer domains (e.g., near the linked 5' ends), which may be used for amplification of sequence-ready barcoded constructs produced using the methods of the present disclosure (see, e.g., FIGS. 1A-1G). The length of a primer domain may vary. In some embodiments, a primer domain has a length of 5-50 nucleotides. For example, a primer domain may have a length of 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-40, 25-35, 25-30, 30-40, 30-35 or 35-40 nucleotides. In some embodiments, a primer domain has a length of 5, 10, 15, 20, 25, 30, 35, 40, 45 or 50 nucleotides. In some embodiments, a primer domain has a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. A primer domain, in some embodiments, is longer than 50 nucleotides, or shorter than 5 nucleotides.

Barcodes and Unique Molecular Identifiers

Systems and methods of the present disclosure, in some embodiments, use a whip molecule in combination with a barcoded nucleic acid. A "barcoded nucleic acid" is a nucleic acid, typically single-stranded, that includes a barcode domain. A "barcode domain" is a domain that includes a nucleotide sequence that can be used to identify the barcoded nucleic acid or to identify a biomolecule(s) to which the barcoded nucleic acid is linked (directly or indirectly linked). A barcoded nucleic acid may include a barcode domain that is unique to that single nucleic acid (among a population of barcoded nucleic acids, the barcode is specific to that one nucleic acid) or a barcode domain that is unique to a subpopulation of nucleic acids (among multiple populations of barcoded nucleic acids, the barcode is specific to a single subpopulation of barcoded nucleic acids). The length of a barcode domain may vary. For example, a barcode domain may have a length of 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-40, 25-35, 25-30, 30-40, 30-35 or 35-40 nucleotides. In some embodiments, a barcode domain has a length of 5, 10, 15, 20, 25, 30, 35, 40, 45 or 50 nucleotides. In some embodiments, a barcode domain has a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. A barcode domain, in some embodiments, is longer than 50 nucleotides, or shorter than 5 nucleotides.

The length of a barcoded nucleic acid itself may vary. In some embodiments, the length of a barcoded nucleic acid is 20-1000 nucleotides. For example, a barcoded nucleic acid may have a length of 20-900, 20-800, 20-700, 20-600, 20-500, 20-400, 20-300, 20-200, 20-100, 20-50 or 20-25 nucleotides. In some embodiments, a barcoded nucleic acid has a length of 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 450 or 500 nucleotides. In some embodiments, a barcoded nucleic acid is longer than 1000 nucleotides.

A barcoded nucleic acid, in some embodiments, further includes a primer domain and an anchor domain that is complementary to one of the anchor domains of a whip molecule. An example of a barcoded nucleic acid is shown in FIG. 1A. The example barcoded nucleic acid shown in FIG. 1A comprises a primer domain at its 5' end, an internal (central) barcode domain and an anchor domain at its 3' end. It should be understood that the barcoded domain need not be centrally located. The 5' end of the barcoded nucleic acid, in this example, is linked to an antibody that recognizes a protein of interest (e.g., a protein associated with genomic DNA). A barcoded nucleic acid may be linked to any biomolecule, as discussed below. The 3' end of the barcoded nucleic acid, in this example, includes an anchor domain that that is complementary to one 3' end of a whip molecule such that the two anchor domains bind to each other to form a paired domain.

Anchor domains may be single-stranded, double-stranded or partially double-stranded (containing a single-stranded and double-stranded nucleic acid). One of the anchor domains shown in FIG. 1A, for example, is partially double-stranded and contains a unique molecular identifier (UNI) ('Anchor 2'). Barcoded nucleic acids typically include a single-stranded anchor domain. An anchor domain may be added to, or may be a component of, a barcoded nucleic acid or a target biomolecule of interest. In FIG. 1A, the anchor domain "Anchor 1" is a component of (is contiguous with) the barcoded nucleic acid, whereas the anchor domain "Anchor 2" was added (ligated) as a component of an adaptor molecule (discussed below) to the genomic DNA fragment, following shearing of the genomic DNA.

Anchor domains, in some embodiments, are used for localizing a target biomolecule(s) of interest. When co-localizing two biomolecules, one of the biomolecules contains an anchor domain complementary to one of the anchor domains of a whip molecule, and the other biomolecule contains an anchor domain complementary to the other of the anchor domains of a whip molecule. When a whip molecule is used in combination with a barcoded nucleic acid linked to a target biomolecule, typically the barcoded nucleic acid contains an anchor domain complementary to one anchor domain of the whip molecule, and another biomolecule contains an anchor domain complementary to the other anchor domain of the whip molecule and has a unique molecular identifier (UMI), as shown, for example, in FIG. 1A. In FIG. 1A, one anchor domain is present on a barcoded nucleic acid linked to an antibody that recognizes a histone, and another anchor domain is present on a genomic DNA fragment. This configuration permits localization of the histone protein to the particular genomic DNA fragment.

In some embodiments, an adaptor molecule comprises a unique molecular identifier (UMI) or other nucleotide sequence or moiety specific to that adaptor molecule, which makes distinct each adaptor molecule in a population (see, e.g., Kivioja, T. et al. *Nat Methods* 2012, 9, 72-4).

Adaptor Molecules

Adaptor molecules are used, in some embodiments, to add an anchor domain or other nucleotide domain to a another nucleic acid molecule. For example, FIG. 1A depicts adaptor molecules at each end of a fragmented piece of chromatin. Each adaptor molecule in FIG. 1A includes an unpaired 3' overhang, which includes an anchor domain, Anchor2. Whether an adaptor is single-stranded, double-stranded, or partially double-stranded (partially single-stranded), depends on the target biomolecule to which the adaptor is being added. Typically, a double-stranded, or partially, double-stranded adaptor is added to the terminus (or termini) of a double-stranded target nucleic acid, and a single-stranded adaptor is added to the terminus of a single-stranded target nucleic acid.

Figure 1D:
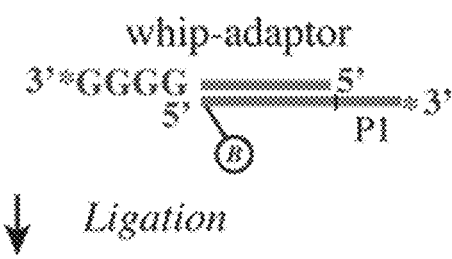

As another example, a "whip-adaptor" molecule is shown in FIG. 1D. This type of adaptor molecule is used, for example, to add a double-stranded domain and a single-stranded homopolymer overhang domain (or other single-stranded nucleotide overhang domain) to a 3' end of an extended whip molecule (e.g., following hybridization to a barcoded nucleic acid, polymerization through the barcoded domain, and dissociation of the resulting partially double-stranded molecule). This whip-adaptor facilitates joining of the two 3' ends of an extended whip molecule to form a circular double-stranded molecule, which may then be isolated, linearized and sequenced, as discussed below.

A homopolymer domain is simply a contiguous stretch of the same nucleotides, such as for example, GGGG. A homopolymer may comprise adenines, guanines, cytosines or thymines (or variants thereof). It should be understood that the homopolymer domain is used to join the 3' ends of the extended whip molecule to each other to permit polymerization to form a circular, double-stranded molecule. Other means of joining the two 3' ends are encompassed by the present disclosure. Thus, the homopolymer domains may be substituted with other complementary nucleotide domains, for example.

Biomolecules

The systems and methods of the present disclosure, in some embodiments, are used to detect biomolecules within close proximity to each other (e.g., 500 nm or less, such as 1, 2, 3, 4, 5, 10, 15, 20, 25, 30, 35, 40, 45, 50, 55, 60, 65, 70, 75, 80, 85, 90, 95, 100, 150, 200, 250, 300, 350, 400, 450 or 500 nm). To detect proteins of interest, for example, a barcoded nucleic acid may be linked (covalently or non-covalently) to a binding biomolecule that binds to the target protein of interest. In some embodiments, the binding biomolecule is an antibody or an antibody fragment. To detect nucleic acids of interest, as another example, a barcoded nucleic acid may include a domain that binds directly to (is complementary to) the target nucleic acid of interest. Alternatively, as yet another example, a barcoded nucleic acid may be linked (covalently or non-covalently) to another nucleic acid that binds to (is complementary to) the target nucleic acid of interest.

A "binding biomolecule" is any biomolecule that binds to another biomolecule. Examples of biomolecules include, without limitation, proteins, nucleic acids, carbohydrates and lipids. Antibody-antigen and receptor-ligand binding partners are common examples of biomolecules that bind to each other (binding biomolecules).

In some embodiments, a target protein of interest is a histone or other protein associated with (e.g., bound to) genomic DNA. Histones are highly alkaline proteins found in eukaryotic cell nuclei that package and order the DNA into nucleosomes (structural units). Histones are the primary protein components of chromatin, functioning as spools around which DNA winds and having a role in gene regulation. In some embodiments, a binding biomolecule is an antibody, or antibody fragment, that binds to a histone. There are five major families of histones: H1/H5, H2A, H2B, H3 and H4. Histones H2A, H2B, H3 and H4 are the core histones, while histones H1 and H5 are the linker histones. Below is a list of human histone proteins. A binding biomolecule may be any biomolecule, e.g., antibody or antibody fragment, that binds to a histone, for example, a histone listed in Table 1.

TABLE 1

Human histone proteins.

| Super family | Family | Sub-family | Members |
|---|---|---|---|
| Linker | H1 | H1F | H1F0, H1FNT, H1FOO, H1FX |
|  |  | H1H1 | HIST1H1A, HIST1H1B, HIST1H1C, HIST1H1D, HIST1H1E, HIST1H1T |
| Core | H2A | H2AF | H2AFB1, H2AFB2, H2AFB3, H2AFJ, H2AFV, H2AFX, H2AFY, H2AFY2, H2AFZ |
|  |  | H2A1 | HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM |
|  |  | H2A2 | HIST2H2AA3, HIST2H2AC |
|  | H2B | H2BF | H2BFM, H2BFS, H2BFWT |
|  |  | H2B1 | HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO |
|  |  | H2B2 | HIST2H2BE |
|  | H3 | H3A1 | HIST1H3A, HIST1H3B, HIST1H3C, HIST1H3D, HIST1H3E, HIST1H3F, HIST1H3G, HIST1H3H, HIST1H3I, HIST1H3J |
|  |  | H3A2 | HIST2H3C |
|  |  | H3A3 | HIST3H3 |
|  | H4 | H41 | HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L |
|  |  | H44 | HIST4H4 |

Methods and Systems

Figure 1E:
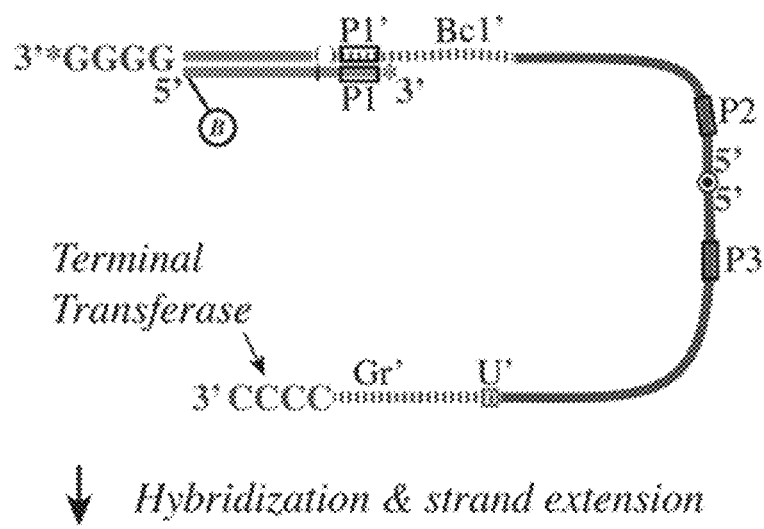
Figure 1F:
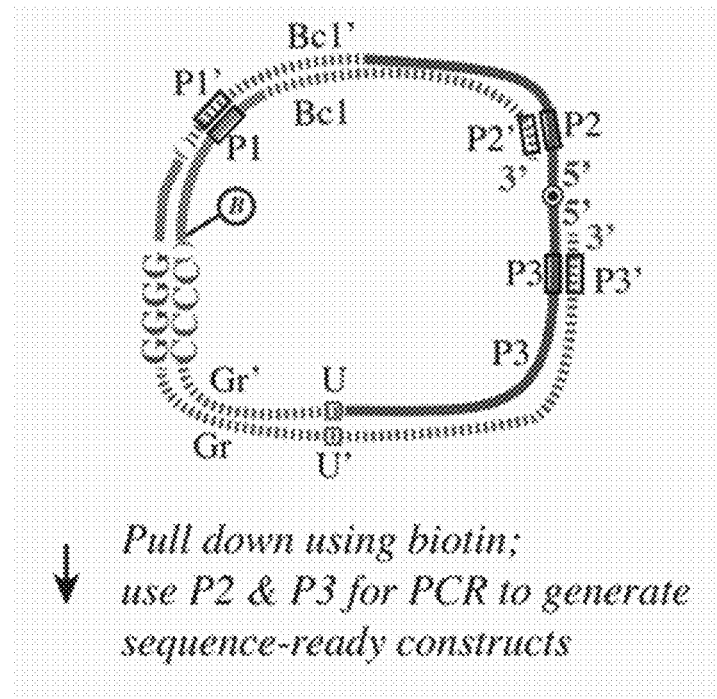
Figure 1G:
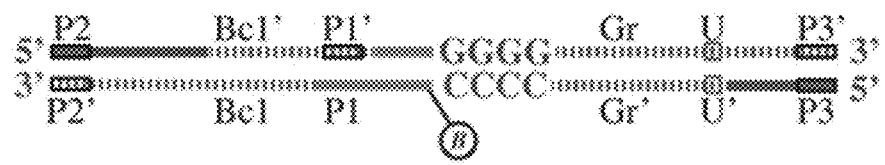

Methods and systems provide herein use nucleic acid whip molecules to detect two (or more) molecules within close proximity (e.g., 500 nm or less) to each other. FIGS. 1A-1G illustrate an example of the major steps of a detection method of the present disclosure for detecting DNA-associated proteins bound to chromatin. Sheared chromatin is incubated with multiple antibodies, and each antibody is labeled with a single-stranded nucleic acid that includes a primer region (Primer 1), a unique barcode (Barcode 1, 2, etc.) and an anchor domain (Anchor 1) (FIG. 1A). The ends of the DNA molecule in each fragment are ligated to adaptors (e.g., library adaptors) that include a different anchor domain (Anchor 2) and a unique molecular identifier (UMI). The whip molecule (the single-stranded nucleic acid having two 3' ends is generated from two nucleic acids covalently bound at the 5' ends by click chemistry, for example; each arm contains a specific primer sequence and, at each 3' end, sequences complementary to the anchor domain it targets. Target sequences are captured by hybridization of the two whip anchor domains (Anc1' and Anc2') to the barcoded nucleic acid-antibody conjugate and the library adaptor 3' overhang, followed by DNA polymerase extension (dashed) at both ends (FIG. 1B). The single-stranded whip with the extensions is separated from the antibody-chromatin complex by denaturation, for example (FIG. 1C). A double-stranded whip-adaptor is then used to bring the two ends of the extended whip together. One adaptor 3' end contains an oligo-G overhang (or other overhang sequence), while the other has a P1 single-stranded overhang and a biotin moiety (for example) linked to the corresponding 5' end (a 'B' inside a circle) (FIG. 1D). Both termini contain cleavable blockers of extension. The adaptor hybridizes to the P1' end of the whip. Then, the other end of the extended whip is 3' modified by terminal transferase to include a stretch of oligo-C (FIG. 1E). The oligo-G and oligo-C ends are used for intra-molecular hybridization, and the free 3' ends of each of the whip arms are then extended using the other arm as a template (FIG. 1F). Finally, the click bond is broken, and the double-stranded fragments are used as a template for generation of a sequencing-ready construct by polymerase chain reaction (PCR), for example, from the primer sequences (P2 and P3) embedded in the original whip (FIG. 1G).

In some embodiments, methods provided herein comprise combining in reaction solution that comprises polymerase and deoxynucleoside triphosphates (dNTPs) (or other nucleoside triphosphates) (a) a single-stranded nucleic acid comprising two 3' ends (whip molecule), wherein each 3' end comprises an anchor domain, (b) a barcoded nucleic acid comprising a primer domain, a barcode domain and a nucleotide domain that is complementary to one of the anchor domains of the single-stranded nucleic acid, wherein the at least one barcoded nucleic acid is linked to a binding biomolecule (e.g., antibody) that binds to a target biomolecule of interest, and (c) a biomolecule (e.g., fragmented chromatin) comprising a nucleotide domain that is complementary to the other of the anchor domains of the single-stranded nucleic acid, thereby forming a reaction mixture.

The reaction solution (and a reaction mixture) may comprise any reagents necessary for nucleic acid hybridization and polymerase-based strand extension. Factors that influence nucleic acid hybridization and polymerization are well-known in the art, including pH, concentration of monovalent cations, salts and buffers, concentration of nucleic acid, concentration and type of polymerase, and concentration of dNTPs.

The reaction solution may comprises any type of polymerase that is capable of extending the length of a whip molecule. Polymerases (e.g., DNA polymerases and RNA polymerases) are well-known in the art and include, for example, prokaryotic polymerases (e.g., Pol I-Pol V) and eukaryotic polymerases (e.g., beta, lambda, sigma, mu, alpha, delta, epsilon, eta, iota, kappa, Rev1, zeta, telomerase, gamma, theta, and reverse transcriptase).

The concentration of nucleoside (deoxyribonucleo side or ribonucleoside) triphosphates (NTPs, including ATP, GTP, TTP/UTP and CTP) may vary. For example, the concentration of NTP (e.g., dNTP) in a reaction solution (e.g., buffer) may be 2 nM-1000 nM, 10 nM-100 nM, or 10 nM-500 nM. In some embodiments, the concentration of NTP in a reaction solution is 2, 5, 10, 25, 50, 100, 150, 200, 300, 500 or 1000 nM.

In some embodiments, the methods comprise incubating a reaction mixture under conditions that result in binding of the single-stranded nucleic acid whip to a barcoded nucleic acid and to a biomolecule (e.g., antibody), and extension of the single-stranded-nucleic acid through the primer domain of the barcoded nucleic acid, thereby producing a partially-double-stranded molecule (a nucleic acid molecule that includes single-stranded and double-stranded domains) (see, e.g., FIGS. 1A and 1B).

Other factors that influence nucleic acid hybridization and polymerization include the duration of incubation and the temperature at which a reaction mixture is incubated. In some embodiments, a reaction mixture is incubated for 20 minutes to 24 hours. For example, a reaction mixture may be incubated for 20, 25, 30, 35, 40, 45, 50 or 55 minutes. In some embodiments, a reaction mixture is incubated for 1, 2, 3, 4, 5, 6, 8, 10, 12, 14, 16, 18, 20, 22 or 24 hours, or longer. The temperature at which a reaction mixture is incubated may range from 4° C. to 65° C., depending on the type of polymerase used, the concentration of dNTP in the reaction mixture, and the concentration and composition of the nucleic acid molecules, for example. In some embodiments, a reaction mixture is incubated a temperature of 4° C., 15° C., 25° C., 30° C., 32° C., 42° C., 50° C., 55° C. or 65° C.

In some embodiments, the methods further comprise incubating in reaction solution the partially-double-stranded molecule under conditions that result in separation of the partially-double-stranded molecule into a barcoded nucleic acid and an extended single-stranded nucleic acid whip comprising a complementary barcode domain and a complementary primer domain, wherein the extended single-stranded nucleic acid whip comprises two 3' ends (see, e.g., FIG. 1C). In some embodiments, conditions that result in separation of nucleic acids include denaturation (melting) conditions. Methods of determining the denaturation temperature, also referred to as melting temperature (Tm), of double-stranded nucleic acids are well-known. The melting temperature (Tm) is the temperature at which the DNA strands are half denatured, meaning half double-stranded, half single-stranded. The percentage of GC content of DNA has a significant effect on Tm. Because G-C pairs form three hydrogen bonds, while A-T pairs form only two, the higher the percentage of GC content, the higher its Tm. Thus, a double-stranded DNA rich in G and C needs more energy to be broken than one that is rich in A and T, meaning higher melting temperature (Tm). Above the Tm, DNA denatures, below it, DNA anneals. Other methods of denaturation or separation of nucleic acids are encompassed by the present disclosure. For example, organic solvents such as dimethyl sulfoxide and formamide, or high pH, may be used to break the hydrogen bonding between DNA strands. Low salt concentration may denature DNA double-strands by removing ions that stabilize the negative charges on the two strands from each other.

The extended single-stranded nucleic acid (whip) may then be incubated in reaction solution that comprises ligase and a nucleic acid adaptor under conditions that result in ligation of the nucleic acid adaptor to the extended whip. A ligase is an enzyme that catalyzes the joining of two nucleic acid molecules by forming a new chemical bond. The nucleic acid adaptor, referred to as a whip-adaptor, typically comprises (i) a paired (double-stranded) nucleotide sequence flanked by (ii) an unpaired (single-stranded) primer domain that binds to the complementary primer domain of the extended single-stranded nucleic acid and (iii) an unpaired homopolymer domain (see, e.g., FIG. 1D). Joining of the whip-adaptor to the extended whip molecule produces a homopolymer domain at one of the 3' ends of the extended whip molecule (see, e.g., FIGS. 1D and 1E). Another homopolymer domain is also added to the other 3' of the extended whip molecule using, for example, a terminal transferase.

Thus, in some embodiments, the methods further comprise incubating in reaction solution that comprises a terminal transferase the extended whip molecule comprising a homopolymer domain, under conditions that results in addition of nucleotides (e.g., deoxynucleotides) to the other 3' end of the extended whip molecule to produce a homopolymer domain at the other 3' end of the extended whip molecule, wherein the two homopolymers domains of the extended whip molecule are complementary to each other.

After the terminal homopolymer domains are added to the extended whip molecule, the domains are hybridized to each other to form a circular molecule. Thus, in some embodiments, the methods further comprise incubating a reaction mixture containing the extended whip molecule having two terminal homopolymers domains in the presence of polymerase and dNTPs under conditions that result in nucleic acid hybridization and polymerization for a time sufficient to produce a circular, double-stranded nucleic acid (see, e.g., FIG. 1F).

This circular nucleic acid may then be isolated and 'decoded' to determine which biomolecules were within close proximity to each other. In some embodiments, the circular, double-stranded nucleic acids are isolated, for example, using a pull-down assay. In some embodiments, the circular nucleic acids are tagged with a binding partner molecule (e.g., biotin), as described above, and are isolated by contacting the circular nucleic acids with a cognate binding partner (e.g., streptavidin). Other pull-down systems are also encompassed by the present disclosure. For example, antigen/antibody-based or magnetic bead-based (e.g., SNAP-Capture Magnetic Beads, Protein G Magnetic Beads, or Amylose Magnetic Beads) pull-down assays may be used.

Following isolation/pull-down of the circular nucleic acids, the nucleic acids are linearized, typically by breaking the click bonds that join the two 5' ends of the whip molecule component (see, e.g., Brantley J N, et al. *Science,* 2011, 333, 1606).

Thus, in some embodiments, the methods further comprise incubating in reaction solution the circular, double-stranded nucleic acid under conditions that result in linearization of the circular, double-stranded nucleic acid, thereby producing a linear double-stranded nucleic acid comprising a barcode domain.

In some embodiments, the linearized barcoded construct is amplified and sequenced (e.g., using Next-Gen Sequencing (NGS)). Any nucleic acid amplification assay may be used. For example, a polymerase chain reaction (PCR) may be employed using primers that are complementary to the primer domains present in the initial whip molecule (which forms a component of the linearized barcoded construct. Other nucleic acid amplification methods are encompassed by the present disclosure.

The biomolecule detection systems provided herein may include a plurality of whip molecules and a plurality of barcoded nucleic acids. These systems are useful for detecting a number of different interactions among various target biomolecules of a particular population or cell or other environment. A plurality of molecules include at least to molecules. In some embodiments, a plurality of molecules (e.g., whip molecules and/or barcoded nucleic acids) includes 10-100, 10-1000 or 10-10000 molecules. In some embodiments, a plurality of molecules includes 10, 20, 30, 40, 50, 60, 70, 80, 90, 100, 200, 300, 400, 500, 1000, 2000, 5000 or 10000 molecules.

Mapping Genomic Organization

Mapping the genomic organization of modified histones and defining locations of DNA binding proteins is important for understanding the regulatory mechanisms governing cellular states. Understanding chromatin structure and its functional roles has been revolutionized by access to powerful analytical approaches such as chromatin immunoprecipitation (ChIP), and even more so through the use of high throughput DNA sequencing as a readout (ChIP-seq). Nonetheless, ChIP-seq has limitations including (i) limited efficiency of the immunoprecipitation step; (ii) inability to profile several epitopes simultaneously in one sample; and (iii) the output represents an average signal from multiple cells. Because of these limitations of current ChIP-based methods, existing ChIP-seq datasets cannot unambiguously represent the combinatorial states of histone modifications and DNA-associated proteins within the cell without significant and costly follow up work. The technology of the present disclosure may be used to overcome these limitations and readily decode the combinatorial signatures in normal, developmental and disease states, thereby greatly advancing the field of chromatin biology. The system, methods and compositions provided herein enable one to simultaneously study the organization of multiple DNA binding proteins from a single sample and to identify instances where these proteins are bound to the same genomic molecule originating from a single cell.

DNA binding proteins, particularly chromatin regulators (CRs), determine epigenetic states that are critical to sustaining cell fates, and thus to modulating stem cell pluripotency, cellular and tissue differentiation as well as organismal homeostasis. Such cellular processes require a regulated set of events that are determined by the precise and coordinated function of different CRs. Indeed, defects in epigenetic factors represent one of the major causes behind numerous diseases, including cancer and neurodegenerative syndromes. As such, the technology as provided herein, in some embodiments, may be used to observe and assess the different combinatorial signatures established during differentiation, and to assess how these signatures may go awry in disease. This high-resolution mapping, in some embodiments, serves as a guide for designing therapeutic approaches targeting these devastating diseases.

EXAMPLES

The Examples discussed below are directed to identifying precise patterning of genome-wide chromatin signatures by assessing the organization of DNA binding proteins from a single sample and identifying instances where these proteins are bound to the same genomic molecule originating from a single cell. Tables 2-4 provides examples of nucleic acid molecules used in the experiments described below.

Example 1. Mapping Multiple Epitopes from a Single Sample

A methodology is developed, which is aimed at overcoming the limitations encountered in standard ChIP-seq approaches. The method, referred to as 'Whip-seq', is based, in part, on a unique single-stranded DNA molecule having two 3' ends (a 'whip'). The whip molecule functions as a proximity detector between, for example, a specific antibody bound to an epitope and the associated genomic DNA. By doing so, it also obviates an immunoprecipitation step. Further, to carry out multiplex genomic localization of multiple DNA-associated proteins from a single sample, DNA barcoded antibodies are used in the Whip-seq method. Using Unique Molecular Identifiers (UMIs), Whip-seq identifies co-localized proteins on the same original genomic DNA molecule. The simultaneous interrogation of DNA-associated proteins in each individual sample enables inference of protein complex dynamics to unprecedented sensitivity.

Figure 2A:
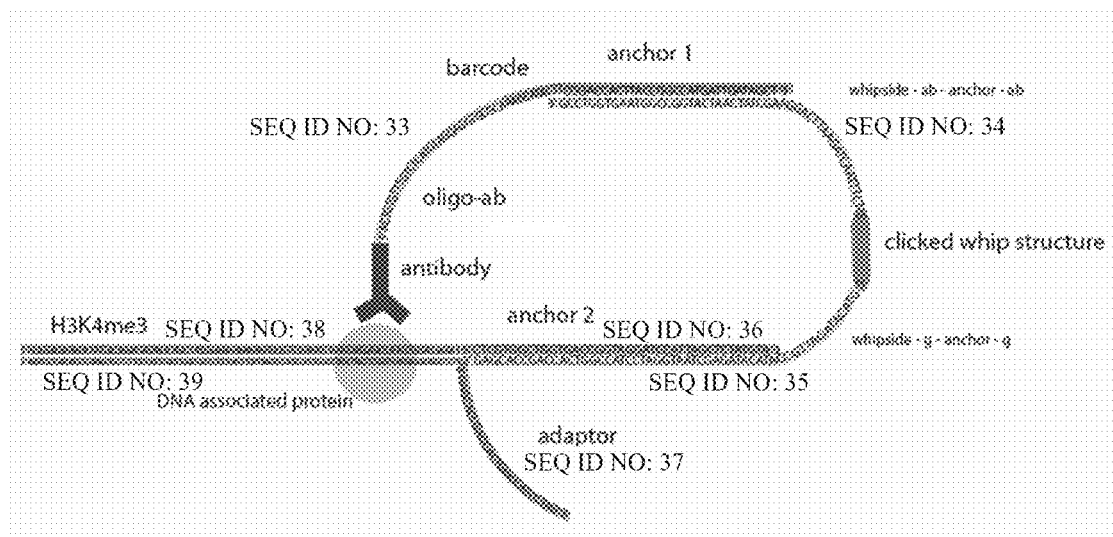
FIG. 2A shows an example of a whip molecule bound to a barcoded nucleic acid and genomic, fragmented DNA containing an adaptor molecule, similar to the schematic shown in FIG. 1B.
Figure 2B:
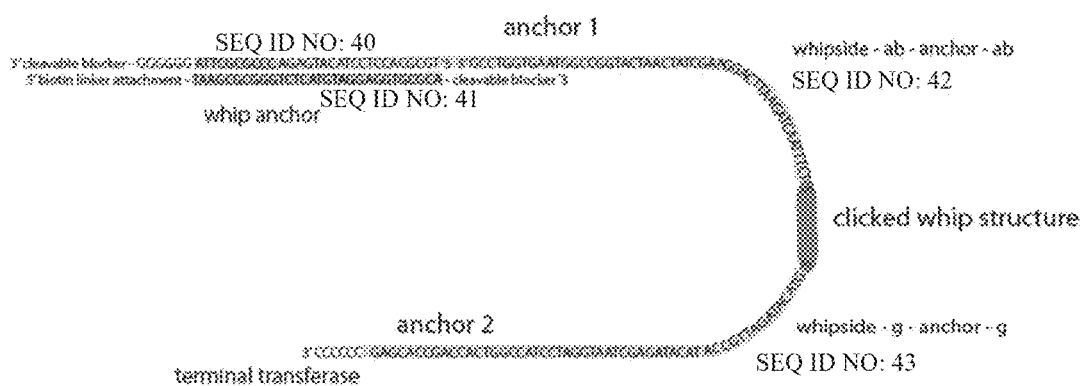
FIG. 2B shows an example of a whip molecule following dissociation from the barcoded nucleic acid and the genomic DNA and following addition of a whip anchor and a homopolymer via a terminal transferase reaction.

A whip molecule was synthesized, assembled by click chemistry. Then, using an nucleic acid designed with the corresponding anchor sites, the whip molecule properly hybridized and successfully provided a template for polymerase strand extensions. Adaptors were ligated to cross-linked chromatin (see, e.g., Lara-Astiaso et al. *Science* 345, 943-9 (2014)), and libraries were generated from chromatin immobilized with an antibody for H3K27ac. Results were highly similar to ChIP-seq data generated with the same epitope (see FIGS. 4A-2C).

To evaluate epitope multiplexing, nucleic acid-tagged antibodies targeting each of the 4 histone proteins in the assembled nucleosomes are used.

Example 2. Computation Framework to Analyze Whip-Sew Datasets

To identify and evaluate the specific association of antibody barcodes to genomic fragments, a modified computational framework is used (Shishkin et al. *Nat Methods* 12, 323-5 (2015)), which enables an assessment of key metrics, such as the percentage of reads containing valid barcodes, whether barcodes occur in the expected location and frequency, and the association of a particular UMI with a specific genomic region.

Pools of barcodes with control constructs and antibodies are tested to identify a set of sequences that provides even representation and can be optimally demultiplexed with a tolerance for sequence errors.

The specificity of the association between antibody and barcode during the Whip-seq process is also evaluated. For example, the histone modification H3K9me3 occurs within repressed regions of the genome while H3K9ac (that occurs on the same lysine residue) and H3K4me3 are associated with active regions. These active and repressive marks are thus not expected to co-occur (Binda, *Epigenetics* 8, 457-63 (2013)). The fidelity of the barcode ligation is tested by quantifying the degree of co-occurrence of these marks in the Whip-seq process as compared to control ChIP-seq benchmarks.

To systematically evaluate the Whip-seq process, Whip-seq data is compared to ChIP-seq benchmark data generated in parallel on the same samples. Additionally, six key histone modifications—H3K4me1, H3K4me3, H3K9me3, H3K27ac, H3K27me3, and H3K36me3—are targeted. Each modification is measured with two to four technical replicates using two different antibodies. These epitopes represent both open and closed chromatin conformations and have distinct and well-characterized localization patterns, making them ideal for assessing the specificity of Whip-seq in various genomic contexts. In particular, the reference dataset provides a truth set for areas of the genome containing co-occurring histone modifications, which are candidates for marks co-localized on the same DNA fragment. They also provide a means to identify off-target artifacts that might be introduced when mapping with multiple antibodies at once in the Whip-seq approach. Finally, it ensure that the protocol is released with a comprehensive dataset against which users can baseline their own work.

Example 3. Identification and Characterization of Protein Complexes

Enabling identification and characterization of protein complexes that are located on the same original genomic DNA molecule, in some instances, requires multiple rounds of whip hybridization-extension reactions, which in turn requires stabilization of the antibodies to their targets, for example, by an additional crosslinking step. First, multiple antibodies are used in one reaction, and the whip hybridization-extension reaction is not iterated. Next, a rare cutting restriction enzyme is used to remove the extended whip, allowing for the next one to hybridize and removing any antibody-barcoded nucleic acid that went through the extension reaction. The restriction enzyme cuts only the antibody-barcoded nucleic acid that becomes double stranded through the extension, leaving behind the non-extended single-stranded ones. This enables the performance of several cycles and, using UMIs, identifies localization of complexes originating from the same genomic molecule. Finally, the whip hybridization-extension reaction is performed multiple times using a cycling method that is based on isothermal helicase dependent amplification (Jeong et al. *Cell Mol Life Sci* 66, 3325-36 (2009)) avoiding the thermal stress of temperature cycling. A helicase is used to denature the whips, and thus renews the template for other whips to anneal and extend. This increases the ability of Whip-seq to efficiently detect original molecules that were bound by multiple proteins.

Example 4. Analyzing Co-Association of Chromatin Regulators

The Whip-seq method is used to investigate chromatin dynamics in mouse embryonic stem (mES) cells that are responding to environmental queues. The co-binding of multiple chromatin regulators (CRs), transcription factors and histones bearing specific modifications is assessed in mES cells. CR Sirt6, both in human and mouse, is a histone deacetylase that responds dynamically to and plays key roles in regulation of environmental changes, glucose metabolism and differentiation. Sirt6 is associated with multiple protein complexes that include transcription factors and chromatin modulators. However, the genomic organization of these complexes remains largely unknown. The Whip-seq method is used to assess the genomic organization of the transcription machinery components. By mapping co-binding events of Sirt6 with other DNA binding proteins on the same original DNA molecule, congruent map of these complexes is drafted, and their dynamic regulation upon metabolic and environmental cues is elucidated.

Mapping co-binding events of Sirt6 and transcription machinery components on the same original DNA molecule and doing this over different conditions elucidates the dynamic regulation in response to metabolic and environmental cues. The relationship between these different components are evaluated in ES cells under nutrient stress conditions (e.g., with or without glucose depletion), or following enforced differentiation (e.g., retinoic acid treatment). Whip-seq and multiple antibodies are used to study the co-binding of Sirt6 with RNAPol-II, Ser5-Pol-II, Ser2-Pol II, pausing promoting factors (NELF, DSIF) and the Super Elongation Complex (SEC), H3K36me3 and H3K79me (histone marks previously associated with elongation), and H3K56Ac/H3K9Ac (histone modifications regulated by Sirt6). Most of the antibodies targeting these epitopes have been validated. The data obtained with Whip-seq are compared to data obtained by ChIP-seq.

Co-binding of factors in specific loci are also analyzed using immuno-FISH (e.g., Goren et al. *Genes Dev* 22, 1319-24 (2008) and Mostoslaysky et al. *Nature* 414, 221-5 (2001)). For CR epitopes without previously validated monoclonal antibodies, an automated ChIP-seq approach is used to identify certain conditions (Etchegaray et al. *Nat Cell Biol* 17, 545-57 (2015)).

TABLE 2

| Sequence Name | Sequence '5-'3 | Length |
|---|---|---|
| Whipside Oligonucleotides | | |
| whipside-ab - anchor-ab (MspI) | azide-functionalized 5' end - TCTTTAACTAGAATTCAGGAAGCTAT CAAT - CATGGCCGGTAAGTGGTCCG (SEQ ID NO: 1) | 50 |
| whipside-g - anchor-g (MspI) | alkyne-functionalized 5' end - GTACATAGATTGCCATACATAGAGCT AATG - GATCCTACCGGTCACCAGCC ACGAG (SEQ ID NO: 2) | 55 |
| Splint Oligonucleotides | | |
| anchor-ab' (MspI) - splint-ab (EcoRI) | azide-functionalized 5' end - ATCGCAGTCCTTCACACCGTTCTG TAGTTCGATATTCACA - CGGACCACTTACCGGCCATG (SEQ ID NO: 3) | 50 |
| anchor-g'(MspI) - splint-g (EcoRI) | alkyne - functionalized 5' end - GCACATGTTTATCCGATCTTTATCA CGAATTCGATTGATT - CTCGTGGCTGGTGACCGGTAGGATC (SEQ ID NO: 4) | 55 |
| Adaptors | | |
| adaptor-a | CTCGTGGCTGGTGACCGGTAGGATC - CATTA (SEQ ID NO: 28) | 30 |
| adaptor-c | ACCAGCCACGAG*T with phosphothioate bond (SEQ ID NO: 5) | 12 |

TABLE 2-continued

| Sequence Name | Sequence '5-'3 | Length |
|---|---|---|
| | Primers for Adaptors | |
| primer-adaptor1 | TAC CGG TCA CCA GCC ACG AG (SEQ ID NO: 6) | 20 |
| primer-adaptor2 | GAT CCT ACC GGT CAC CAG CC (SEQ ID NO: 7) | 20 |
| primer-adaptor3 | TAATGGATCCTACCGGTCAC (SEQ ID NO: 8) | 20 |

TABLE 3

| Sequence Name | Sequence '5-'3 | Melting Temp. | GC Content | Length |
|---|---|---|---|---|
| whipside-ab (EcoRI) | TCTTTAACTAGAATTCAGGAAGCTATCAAT (SEQ ID NO: 9) | | | 30 |
| whipside-g | GTACATAGATTGCCATACATAGAGCTAATG (SEQ ID NO: 10) | | | 30 |
| anchor-ab (MspI) | CATGGCCGGTAAGTGGTCCG (SEQ ID NO: 11) | | | 20 |
| anchor-g (MspI) | GATCCTACCGGTCACCAGCCACGAG (SEQ ID NO: 12) | | | 25 |
| splint-ab (EcoRI) | TTCACACCGATCTGTAGATCAATGATCAGA (SEQ ID NO: 13) | | | 30 |
| splint-g (EcoRI) | ATCCAACCTTTATCACGAATTCGATTGATT (SEQ ID NO: 14) | | | 30 |
| EcoRIsite | GAATTC (SEQ ID NO: 15) | | | 6 |
| MspI | CCGG (SEQ ID NO: 16) | | | 4 |
| HindIIIsite | AAGCTT (SEQ ID NO: 17) | | | 6 |
| whipside-ab - anchor-ab (MspI) | azide-functionalized 5' end - TCTTTAACTAGAATTCAGGAAGCTATCAAT - CATGGCCGGTAAGTGGTCCG (SEQ ID NO: 18) | 66.6 | 44 | 50 |
| whipside-g - anchor-g (MspI) | alkyne-functionalized 5' end - GTACATAGATTGCCATACATAGAGCTAATG - GATCCTACCGGTCACCAGCCACGAG (SEQ ID NO: 19) | 68.3 | 49.1 | 55 |
| anchor-ab' (MspI) - splint-ab (EcoRI) | azide-functionalized 5' end - ATCGCAGTCCTTCACACCGTTCTGTAGTTCGATATTCACA - CGGACCACTTACCGGCCATG (SEQ ID NO: 20) | 74.9 | 52 | 60 |
| anchor-g' (MspI) - splint-g (EcoRI) | alkyne - functionalized 5' end - GCACATGTTTATCCGATCTTTATCACGAATTCGATTGATT - CTCGTGGCTGGTGACCGGTAGGATC (SEQ ID NO: 21) | 73.5 | 46 | 65 |

TABLE 4

| Sequence Name | Sequence '5-'3 | Length |
|---|---|---|
| whipside-ab (EcoRI) | TCTTTAACTAGAATTCAGGAAGCTATCAAT (SEQ ID NO: 22) | 30 |
| whipside-g | GTACATAGATTGCCATACATAGAGCTAATG (SEQ ID NO: 23) | 30 |
| anchor-ab (MspI) | CATGGCCGGTAAGTGGTCCG (SEQ ID NO: 24) | 20 |
| anchor-g (MspI) | GATCCTACCGGTCACCAGCCACGAG (SEQ ID NO: 25) | 25 |

TABLE 4-continued

| Sequence Name | Sequence '5-'3 | Length |
|---|---|---|
| whipside-ab - anchor-ab (MspI) | azide-functionalized 5' end - TCTTTAACTAGAATTCAGGAAGCTATC AAT - CATGGCCGGTAAGTGGTCCG (SEQ ID NO: 26) | 50 |
| whipside-g - anchor-g (MspI) | alkyne-functionalized 5' end - GTACATAGATTGCCATACATAGAGCTA ATG - GATCCTACCGGTCACCAGCCAC-GAG (SEQ ID NO: 27) | 55 |
| adaptor-a | CTCGTGGCTGGTGACCGGTAGGATC - CATTA (SEQ ID NO: 28) | 30 |
| adaptor-c | ACCAGCCACGAG*T with phosphothioate bond (SEQ ID NO: 29) | 12 |
| primer-adaptor1 | TACCGGTCACCAGCCACGAG (SEQ ID NO: 30) | 20 |
| primer-adaptor2 | GATCCTACCGGTCACCAGCC (SEQ ID NO: 31) | 20 |
| primer-adaptor3 | TAATGGATCCTACCGGTCAC (SEQ ID NO: 32) | 20 |

Example 5

Figure 4A:
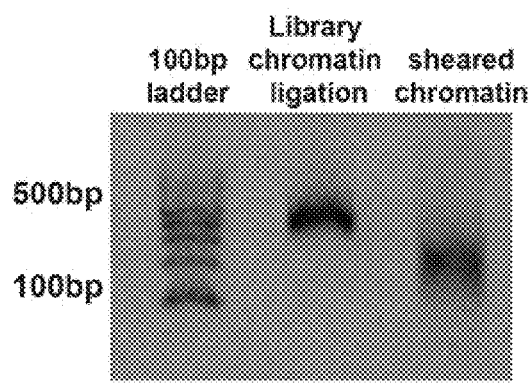
FIGS. 4A-4C show data relating to the ligation of adaptors to cross-linked chromatin.
Figure 4B:
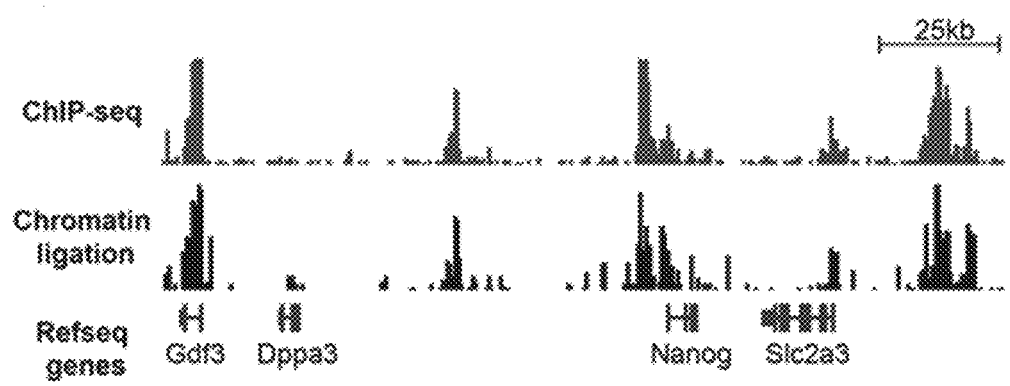
Figure 4C:
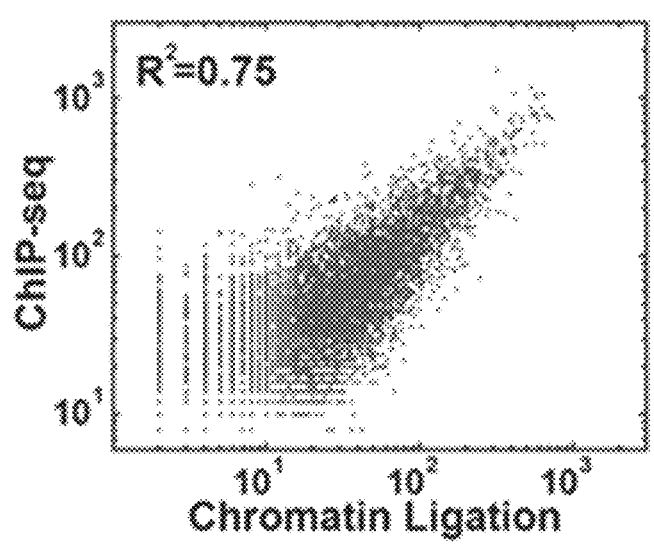
Figure 5:
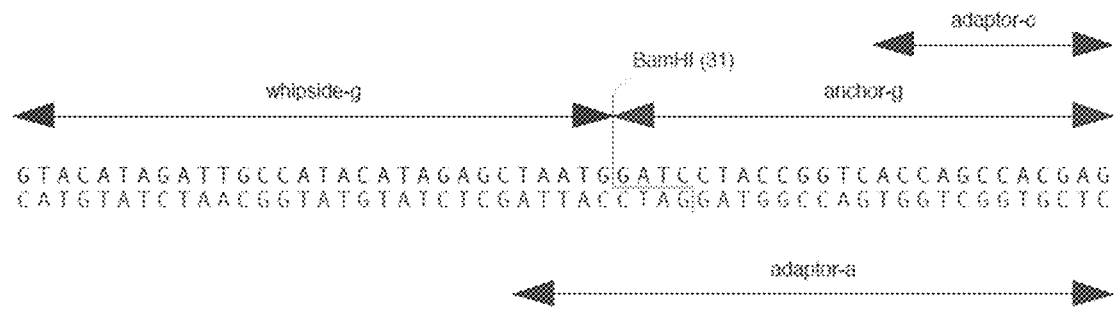
FIG. 5 shows an example of a whip adaptor molecule. The sequences correspond to SEQ ID NO: 54 and 55 from top to bottom.
Figure 6:
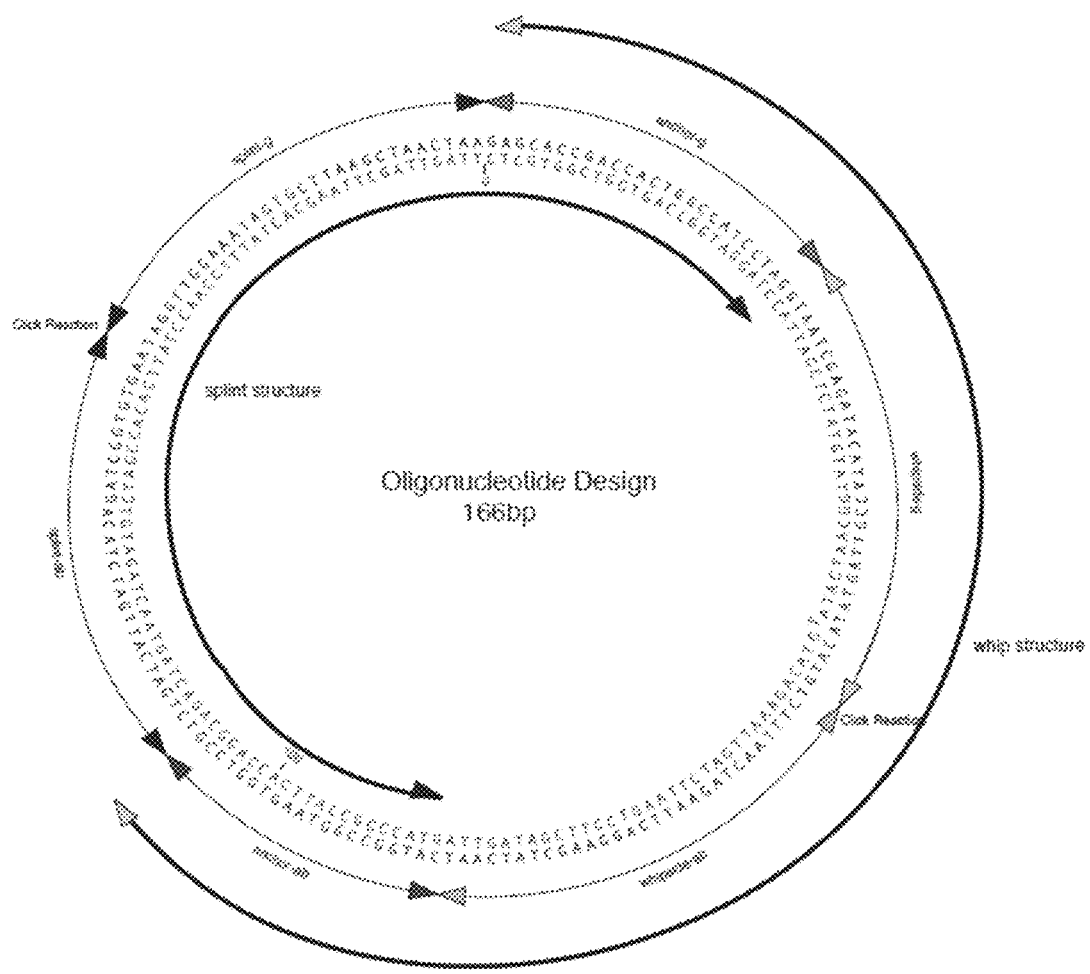
FIG. 6 shows an example of a whip molecule bound to a whip splint molecule. The sequences correspond to SEQ ID NO: 56 (inside strand) and 57 (outside strand).

A H3K4me3 peptide connected to a 125 bp synthetic oligonucleotide (see U.S. Pat. No. 9,175,043, incorporated herein by reference) was used to represent chromatin to show the basic process of capturing sequence data using the method as provided herein. The H3K4me3 peptide can be captured by the antibody, and the entire conjugate is synthetic. This demonstration process included several steps:

(I) Demonstration that adapter ligation works with crosslinked DNA: see Example 1, FIGS. 4A-4C.

(II) Demonstration that the adapters can ligate to the Internal Standard (IS) molecule (see U.S. Pat. No. 9,175,043 for IS details):

To show that the adaptors can be ligated to the IS, the same protocol described above was followed. The success was measured by performing a PCR using primers that amplify the fragment from the adaptors. The correct size fragment was obtained following the PCR (187 bp fragment; FIG. 7A). A gel extraction was performed on the 187 fragment and PCR amplified with the primer (FIG. 7B). Sanger sequencing was performed using primers that span the adapter and IS, since it is the same adapter on both ends. The product was also cut with TaqaI, yielding 134 bp and 53 bp bands (FIG. 7C).

(III) Demonstration of oligonucleotide tagging of antibodies:

Another component of the process was to generate an antibody that is covalently linked to an oligonucleotide. The THUNDER-LINK® kit was used. The objective was to show an ability to covalently bind oligonucleotides (designed with unique barcodes) to antibodies targeting specific antigens researched using ChIP-seq. Results are shown in FIGS. 8A and 8B.

Figure 9:
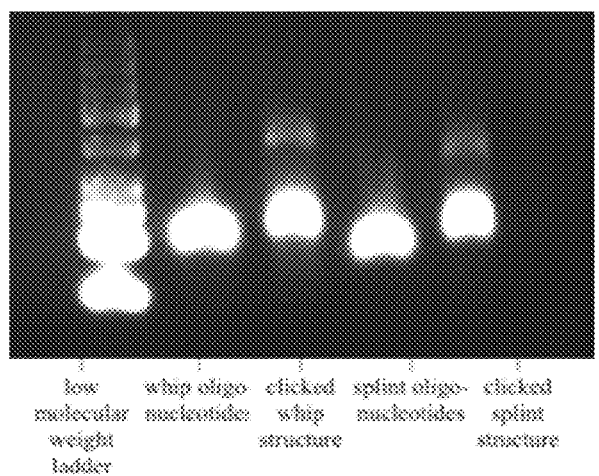
FIG. 9 shows an image of a gel showing two samples (whip and splint) used to demonstrate reproducibility of click reaction success. From left to right: low molecular weight ladder, whip oligonucleotides, clicked whip structure, splint oligonucleotides, clicked splints structure (as an additional demonstration). Single oligonucleotides are 50-60 bases and the clicked structure is 100+ bases.

(IV) Demonstration that the 5' ends of oligonucleotides can be linked: The whip structure is a component of the Whip-seq machinery. In order for the whip to function as a proximity detector to capture sequences by extension, the whip should exist as a single-stranded molecule with two 3' hydroxyl ends that is built from two oligonucleotides. The objective of this demonstration was to show that a linkage can be formed between the 5' ends of two separate oligonucleotides and form a final product with both ends as 3'. To achieve the development of this structure, a click chemistry protocol was used, with slight modification on the amount of catalyst Cu(II)-TBTA and ascorbic acid in order to increase yield. The click reaction product was extracted using the QIAQUICK® gel extraction kit (FIG. 9).

Figure 10:
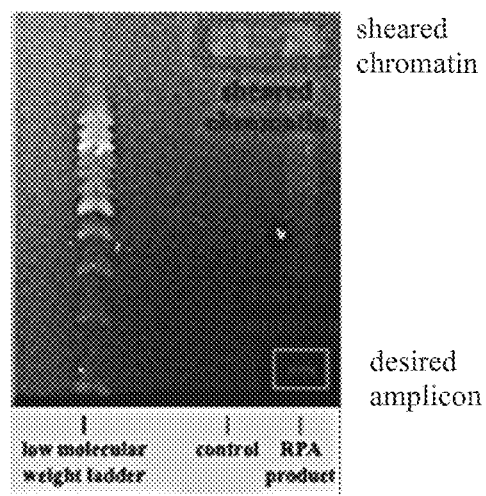
FIG. 10 shows an image of a gel showing mouse genomic DNA incubated with primer-guided recombinase at 37 degrees Celsius for 40 minutes. The desired amplicon is 126 bp long with cut sites for MspI at 33 and 44.

(V) Demonstration of isothermal denaturation:

For the hybridized whip molecule to separate from the genomic structure, isothermal denaturation should be facilitated without disrupting the structure of the ssDNA whip molecule. Recombinase polymerase amplification (RPA) technology permits isothermal amplification of a specified region of a DNA molecule. Pax7 was used as the primer, and the RPA protocol was followed, yielding the desired amplicon (FIG. 10).

Example 6

This Example demonstrates that the method as provided herein can be used with crosslinked chromatin as the input to capture H3K4me3 promoters in mouse ES cells.

1. Use components from above (conjugated oligonucleotide to K4me3 antibody; adapter a and adapter c; WhIP molecule with two 3' ends) to: i) bind tagged antibody to the IS; ii) ligate adapters to the IS; iii) denature and hybridize the whip; and iv) extend whip ends with Klenow to capture antibody and fragment sequences. Reaction are carried out with biotinylated dCTPs to enable capture of extended whips.

2. To evaluate: a) capture the extended sequences that contain the biotinylated dCTPS using streptavidin; and b) perform qPCR on the extensions designed to capture the sequences from the ends of the antibody tag and fragment, along with the adjacent sequences originating from the whip and also sequencing on the Miseq.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A biomolecule detection system comprising
   (a) a single-stranded nucleic acid comprising two 3' ends, wherein one 3' end comprises a first anchor domain and the other 3' end comprises a second anchor domain; and
   (b) a barcoded nucleic acid comprising a primer domain, a barcode domain and a nucleotide domain that is complementary to the first anchor domain of the single-stranded nucleic acid of (a).

2. The system of claim 1, wherein the single-stranded nucleic acid is a conjugate comprising a first nucleic acid strand comprising a 5' end linked to a 5' end of a second nucleic acid strand.

3. The system of claim 2, wherein the 5' end of the first nucleic acid strand is covalently linked to the 5' end of the second nucleic acid strand.

4. The system of claim 3, wherein the single-stranded nucleic acid is produced by reacting an azide group at the 5' end of the first nucleic acid strand with an alkyne group at the 5' end of the second nucleic acid strand.

5. The system of claim 4, wherein the single-stranded nucleic acid of (a) comprises two 5' primer domains.

6. The system of claim 5, further comprising a pair of primers, wherein one of the primers is complementary to one of the primer domains of the single-stranded nucleic acid, and the other primer is complementary to the other primer domain of the single-stranded nucleic acid.

7. The system of claim 1, further comprising a nucleic acid adaptor that comprises (i) a unique molecular identifier and (ii) a nucleotide domain that is complementary to the second anchor domain of the single-stranded nucleic acid of (a).

8. The system of claim 1, further comprising a binding biomolecule that binds to a target biomolecule of interest.

9. The system of claim 8, wherein the binding biomolecule is a nucleic acid or a protein.

10. The system of claim 8, wherein the binding biomolecule is an antibody.

11. The system of claim 1, further comprising a polymerase, a ligase and/or a terminal transferase.

12. The system of claim 1, further comprising a nucleic acid adaptor that comprises (i) a paired nucleotide sequence flanked by (ii) an unpaired primer domain and (iii) an unpaired homopolymer domain.

13. The system of claim 12, wherein the nucleic acid adaptor is linked to biotin.

14. The system of claim 1, further comprising at least two barcoded nucleic acids, wherein each barcoded nucleic acid comprises a primer domain, a barcode domain and a nucleotide domain that is complementary to the first anchor domain of the single-stranded nucleic acid of (a).

15. A method, comprising
   combining in reaction solution that comprises polymerase and nucleoside triphosphates (NTPs) (a) a single-stranded nucleic acid comprising two 3' ends, wherein each 3' end comprises an anchor domain, (b) a barcoded nucleic acid comprising a primer domain, a barcode domain and a nucleotide domain that is complementary to one of the anchor domains of the single-stranded nucleic acid, wherein the at least one barcoded nucleic acid is linked to a binding biomolecule that binds to a target biomolecule of interest, and (c) a biomolecule comprising a nucleotide domain that is complementary to the other of the anchor domains of the single-stranded nucleic acid, thereby forming a reaction mixture; and
   incubating the reaction mixture under conditions that result in binding of the single-stranded nucleic acid of (a) to the barcoded nucleic acid of (b) and to the biomolecule of (c), and extension of the single-stranded-nucleic acid through the primer domain of the barcoded nucleic acid, thereby producing a partially-double-stranded molecule.

* * * * *